United States Patent
Ma et al.

(10) Patent No.: US 9,220,810 B2
(45) Date of Patent: Dec. 29, 2015

(54) MESENCHYMAL STEM CELLS (MSC) EXPANSION METHODS AND MATERIALS

(75) Inventors: Teng Ma, Tallahassee, FL (US); Junho Kim, Tallahassee, FL (US)

(73) Assignee: FLORIDA STATE UNIVERSITY RESEARCH FOUNDATION, INC., Tallahasse, FL (US)

(*) Notice: Subject to any disclaimer, the term of this patent is extended or adjusted under 35 U.S.C. 154(b) by 301 days.

(21) Appl. No.: 13/323,475

(22) Filed: Dec. 12, 2011

(65) Prior Publication Data
US 2012/0178159 A1 Jul. 12, 2012

Related U.S. Application Data

(60) Provisional application No. 61/421,889, filed on Dec. 10, 2010.

(51) Int. Cl.
| | |
|---|---|
| *C12N 5/02* | (2006.01) |
| *A61L 27/38* | (2006.01) |
| *C12N 5/00* | (2006.01) |
| *C12N 5/0775* | (2010.01) |

(52) U.S. Cl.
CPC ......... *A61L 27/3804* (2013.01); *A61L 27/3895* (2013.01); *C12N 5/0062* (2013.01); *C12N 5/0663* (2013.01); *C12N 2500/02* (2013.01); *C12N 2533/90* (2013.01); *C12N 2539/10* (2013.01)

(58) Field of Classification Search
CPC .................................. A61L 27/14; A61L 27/38
See application file for complete search history.

(56) References Cited

U.S. PATENT DOCUMENTS

| | | | |
|---|---|---|---|
| 5,486,359 A | 1/1996 | Caplan et al. | |
| 6,875,605 B1 | 4/2005 | Ma | |
| 6,943,008 B1 | 9/2005 | Ma | |

OTHER PUBLICATIONS

Aggarwal, S. and Pittenger, MF "Human Mesenchymal Stem Cells Modulate Allogeneic Immune Cell Responses," *Blood*, 2005, vol. 105, No. 4, pp. 1815-1822.
Ankeny, D.P. et at., "Bone Marrow Transplants Provide Tissue Protection and Directional Guidance for Axons after Contusive Spinal Cord Injury in Rats," *Exp. Neurol*, 2004, vol. 190, pp. 17-31.
Baksh, D. et al., "A Non-Contact Suspension Culture Approach to the Culture of Osteogenic Cells Derived from a CD49e$^{low}$ Subpopulation of Human Bone Marrow-Derived Cells, " *Biotechnology and Bioengineering*, 2007, vol. 98, No. 6, pp. 1195-1208.
Banfi, A. et al., "Proliferation Kinetics and Differentiation Potential of Ex Vivo Expanded Human Bone Marrow Stromal Cells: Implications for Their Use in Cell Therapy," *Experimental Hematology*, 2000, vol. 28, pp. 707-715.
Barbash, I.M. et al., "Systemic Delivery of Bone Marrow-Derived Mesenchymal Stem Cells to the Infracted Myocardium: Feasibility, Cell Migration, and Body Distribution," *Circulation*, 2003, vol. 108, pp. 863-868.
Bernardo, M.E. et al. "Human Bone Marrow-Derived Mesenchymal Stem Cells Do Not Undergo Transformation after Long-Term In Vitro Culture and Do Not Exhibit Telomere Maintenance Mechanisms," *Cancer Res*, 2007, vol. 67, No. 19, pp. 9142-9149.
Bruder, S.P. et al., "Growth Kinetics, Self-Renewal, and the Osteogenic Potential of Purified Human Mesenchymal Stem Cells During Extensive Subcultivation and Following Cryopreservation," *J. Cell. Biochem.*, 1997, vol. 64, pp. 278-294.
Buravkova, L.B. and Anokhina, E.B., "Effect of Hypoxia on Stromal Precursors from Rat Bone Marrow at the Early Stage of Culturing," *Bulletin of Experimental Biology and Medicine*, 2007, vol. 143, No. 4, pp. 411-413.
Caplan, A.I. and Dennis, J.E., "Mesenchymal Stem Cells as Trophic Mediators," *Journal of Cellular Biochemistry*, 2006, vol. 98, pp. 1076-1084.
Chen, J. et al., "Intravenous Administration of Human Umbilical Cord Blood Reduces Behavioral Deficits after Stroke in Rats," *Stroke*, 2001, pp. 2682-2688.
Chen, S.L. et al., "Effect on Left Ventricular Function of Intracoronary Transplantation of Autologous Bone Marrow Mesenchymal Stem Cell in Patients With Acute Myocardial Infarction," *Am J Cardiol*. 2004, vol. 94, pp. 92-95.
Chen, X.D. et al., "Extracellular Matrix Made by Bone Marrow Cells Facilitates Expansion of Marrow-Derived Mesenchymal Progenitor Cells and Prevents Their Differentiation Into Osteoblasts," *Journal of Bone and Mineral Research*, 2007, vol. 22, No. 12, pp. 1943-1956.
Dennis, J.E. et al., "Clinical-Scale Expansion of a Mixed Population of Bone Marrow-Derived Stem and Progenitor Cells for Potential Use in Bone Tissue Regeneration," *Stem Cells*, 2007, vol. 25, pp. 2575-2582.
Dezawa, M., et al., "Sciatic Nerve Regeneration in Rats Induced by Transplantation of in vitro Differentiated Bone-Marrow Stromal Cells," *European Journal of Neuroscience*, 2001, vol. 14, pp. 1171-1176.

(Continued)

*Primary Examiner* — Allison Fox
(74) *Attorney, Agent, or Firm* — Saliwanchik, Lloyd & Eisenschenk

(57) ABSTRACT

The subject invention concerns materials and methods for growing and expanding MSC while maintaining their undifferentiated phenotype, self-renewal ability, and/or multi-lineage potential. In one embodiment, a method of the invention comprises i) seeding freshly isolated MSC on a planar surface or a 3-D scaffold and growing the cells under physiological or low $O_2$ tension for a period of time sufficient to support formation of 3-D ECM network; ii) decellularizing the planar surface or 3-D scaffold; and iii) reseeding the decellularized planar surface or 3-D scaffold with MSCs, whereby the reseeded MSCs can be grown on the scaffold and maintain an undifferentiated phenotype. In one embodiment, the 3-D scaffold comprises or is composed of PET. In one embodiment, the MSC are human MSC (hMSC).

22 Claims, 14 Drawing Sheets
(6 of 14 Drawing Sheet(s) Filed in Color)

(56) References Cited

OTHER PUBLICATIONS

D'Ippoolito, G. et al., "Sustained Stromal Stem Cell Self-Renewal and Osteoblastic Differentiation During Aging," *Rejuvenation Research*, 2006, vol. 9, No. 1, pp. 10-19.
Discher, D.E., et al., "Growth Factors, Matrices, and Forces Combine and Control Stem Cells," *Science*, 2009, vol. 324, pp. 1673-1677.
Fehrer, C. et al., "Reduced Oxygen Tension Attenuates Differentiation Capacity of Human Mesenchymal Stem Cells and Prolongs their Lifespan," *Aging Cell*, 2007, vol. 6, pp. 745-757.
Ferrari, G. et al., "Muscle Regeneration by Bone Marrow-Derived Myogenic Progenitors," *Science*, 1998, pp. 1528-1530.
Furlani, D. et al., "Is the Intravascular Administration of Mesenchymal Stem Cells Safe? Mesenchymal Stem Cells and Intravital Microscopy," *Microvascular Research*, 2009, vol. 77, pp. 370-376.
Gnecchi, M. et al., "Evidence Supporting Paracrine Hypothesis for Akt-Modified Mesenchymal Stem Cell-Mediated Cardiac Protection and Functional Improvement," *FASEB J.*, 2006, vol. 20, pp. 661-669.
Grayson, W.L. et al., "Human Mesenchymal Stem Cells Tissue Development in 3D PET Matrices," *Biotechnology Progress*, 2004, vol. 20, pp. 905-912.
Grayson, W.L., et al., "Effects of Hypoxia on Human Mesenchymal Stem Cell Expansion and Plasticity in 3D Constructs," *J. Cell. Physiol*, 2006, vol. 207, pp. 331-339.
Grayson, W.L. et al., "Hypoxia Enhances Proliferation and Tissue Formation of Human Mesenchymal Stem Cells," *Biochem Biophys Res Commun*, 2007, vol. 358, pp. 948-953.
Hofstetter, C.P., et al. "Marrow Stromal Cells form Guiding Strands in the Injured Spinal Cord and Promote Recovery," *Proc Natl Acad Sci*, 2002, vol. 99, No. 4, pp. 2199-2204.
Honczarenko, M., et al., "Human Bone Marrow Stromal Cells Express a Distinct Set of Biologically Functional Chemokine Receptors," *Stem Cells*, 2006, vol. 24, pp. 1030-1041.
Karp, J.M. and Teo, G.S.L, "Mesenchymal Stem Cell Homing: The Devil is in the Details," *Cell Stem Cell.*, 2009, vol. 4, pp. 206-216.
Katritsis, D.G., et al. "Transcoronary Transplantation of Autologous Mesenchymal Stem Cells and Endothelial Progenitors into Infarcted Human Myocardium," *Catheter Cardiovasc Interv.*, 2005, vol. 65, pp. 321-329.
Keith, B. and Simon, M.C., "Hypoxia-Inducible Factors, Stem Cells, and Cancer," *Cell.*, 2007, vol. 129, pp. 465-472.
Kretlow, J.D., et al., "Donor Age and Cell Passage Affects Differentiation Potential of Murine Bone Marrow-Derived Stem Cells," *BMC Cell Biology*, 2008, vol. 9, No. 60, pp. 1-13.
Klein, G., "The Extracellular Matrix of the Hematopoietic Microenvironment," *Experientia*. 1995, vol. 51, pp. 914-926.
Koc, O.N., et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," *J Clin Oncol.*, 2000, vol. 18, No. 2, 307-316.
Kofoed, H., et al., "Bone-Marrow Circulation after Osteotomy—Blood Flow, $pO_2$, $pCO_2$, and Pressure Studied in Dogs," *Acta Orthop Scand.*, 1985, vol. 56, pp. 400-403.
Kuhn, N.Z. and Tuan, R.S. "Regulation of Stemness and Stem Cell Niche of Mesenchymal Stem Cells: Implications in Tumorigenesis and Metastasis" *J Cell Physiol.*, 2010, vol. 222, pp. 268-277.
Lasala, G.P., et al., "Combination Stem Cell Therapy for the Treatment of Severe Limb Ischemia: Safety and Efficacy Analysis," *Angiology*, 2010, vol. 61, No. 6, 551-556.
Lazarus, H.M. et al., "Cotransplantation of HLA-Identical Sibling Culture-Expanded Mesenchymal Stem Cells and Hematopoietic Stem Cells in Hematologic Malignancy Patients," *Biol Blood Marrow Transplant*, 2005, vol. 11, pp. 389-398. (Abstract only).
Le Blanc, K., et al., "Mesenchymal Stem Cells Inhibit and Stimulate Mixed Lymphocyte Cultures and Mitogenic Responses Independently of the Major Histocompatibility Complex," *Scand J. Immunol*, 2003, vol. 57, pp. 11-20.

Lee, J.S., et al. "A Long-Term Follow-Up Study of Intravenous Autologous Mesenchymal Stem Cell Transplantation in Patients With Ischemic Stroke," *Stem Cells*, 2010, vol. 28, pp. 1099-1106.
Lennon, D.P., et al. "Cultivation of Rat Marrow-Derived Mesenchymal Stem Cells in Reduced Oxygen Tension: Effects on In Vitro and In Vivo Osteochondrogenesis," *J. Cell Physiol.*, 2001, vol. 187, pp. 345-355.
Li, W.U., et al., "Mesenchymal Stem Cells for Ischemic Stroke: Changes in Effects After ex vivo Culturing," *Cell Transplantation*, 2008, vol. 17, pp. 1045-1059. (Abstract only).
Li, Y., et al., "Effects of Filtration Seeding on Cell Density, Spatial Distribution, and Proliferation in Nonwoven Fibrous Matrices," *Biotechnol. Prog.*, 2001, vol. 17, pp. 935-944.
Liao, T., et al., "*N*-Isopropylacrylamide-Based Thermoresponsive Polyelectrolyte Multilayer Films for Human Mesenchymal Stem Cell Expansion," *Biotechnol. Prog.*, 2010, vol. 26, No. 6, pp. 1705-1713.
Liechty, K.W., et al., "Human Mesenchymal Stem Cells Engraft and Demonstrate Site-Specific Differentiation after in utero Transplantation in Sheep," *Nature Medicine*, 2000, vol. 6, pp. 1282-1286.
Mangi, A.A., et al., "Mesenchymal Stem Cells Modified with Akt Prevent Remodeling and Restore Performance of Infarcted Hearts," *Nature Medicine*, 2003, vol. 9, No. 9, pp. 1195-1201.
Marot, D., et al., "Bone Tissue Engineering with Human Stem Cells," *Stem Cell Research and Therapy*, 2010, vol. 1, pp. 1-10.
Nagaya, N., et al., "Transplantation of Mesenchymal Stem Cells Improves Cardiac Function in a Rat Model of Dilated Cardiomyopathy," *Circulation*, 2005, vol. 112, pp. 1128-1135.
Ohgushi, H., et al., "Repair of Bone Defects with Marrow Cells and Porous Ceramic Experiments in Rats." *Acta Orthop Scand.*, 1989, vol. 60, No. 3, pp. 334-339.
Pereira, R.F., et al., "Marrow Stromal Cells as a Source of Progenitor Cells for Nonhematopoietic Tissues in Transgenic Mice with a Phenotype of Osteogenesis Imperfecta," *Proc Natl Acad Sci USA*, 1998, vol. 95, pp. 1142-1147.
Potier, E. et al., "Hypoxia Affects Mesenchymal Stromal Cell Osteogenic Differentiation and Angiogenic Factor Expression," *Bone*, 2007, vol. 40, pp. 1078-1087.
Prockop, D.J. and Olson, S.D. "Clinical Trials with Adult Stem/Progenitor Cells for Tissue Repair: Let's Not Overlook Some Essential Precautions," *Blood*, 2007, vol. 109, No. 8, pp. 3147-3151.
Prockop, D.J., "Repair of Tissues by Adult Stem/Progenitor Cells (MSCs): Controversies, Myths, and Changing Paradigms," *Molecular Therapy*, 2009, vol. 17, No. 6, pp. 939-946.
Prockop, D.J., et al., "Defining the Risks of Mesenchymal Stromal Cell Therapy," *Cytotherapy*, 2010, vol. 12, pp. 576-578.
Quarto, R., et al. "Repair of Large Bone Defects with the use of Autologous Bone Marrow Stromal Cells," *N Engl J Med*, 2001, vol. 344, pp. 385-386.
Rayment, E.A. and Williams, D.J., "Concise Review: Mind the Gap: Challenges in Characterizing and Quantifying Cell- and Tissue-Based Therapies for Clinical Translation," *Stem Cells*, 2010, vol. 28, pp. 996-1004.
Rombouts, W.J.C. and Ploemacher, R.E., "Primary Murine MSC Show Highly Efficient Homing to the Bone Marrow but Lose Homing Ability Following Culture," *Leukemia*, 2003, vol. 17, pp. 160-170.
Sackstein, R., et al. "Ex Vivo Glycan Engineering of CD44 Programs Human Multipotent Mesenchymal Stromal Cell Trafficking to Bone," *Nature Medicine*, 2008, vol. 14, No. 2, pp. 181-187.
Sadat, S., et al. "The Cardioprotective Effect of Mesenchymal Stem Cells is Mediated by IGF-1 and VEGF," *Biochem Biophys Res Commun*, 2007, vol. 363, pp. 674-679.
Sakai, D., et al., "Regenerative Effects of Transplanting Mesenchymal Stem Cells Embedded in Atelocollagen to the Degenerated Intervertebral Disc," *Biomaterials*, 2006, vol. 27, pp. 335-345.
Salem, H.K. and Thiemermann, C., "Mesenchymal Stromal Cells: Current Understanding and Clinical Status," *Stem Cells*, 2010, vol. 28, pp. 585-596.
Sykova, E., et al., "Bone Marrow Stem Cells and Polymer Hydrogels—Two Strategies for Spinal Cord Injury Repair," *Cell Mol. Neurobiol.*, 2006, vol. 26, Nos. 7-8, pp. 1113-1129.

(56) References Cited

OTHER PUBLICATIONS

Tang, Y., et al., "Transplantation of Bone Marrow-Derived Stem Cells: A Promising Therapy for Stroke," *Cell Transplantation*, 2007, vol. 16, pp. 159-169. (Abstract only).

Toma, C., et al., "Fate of Culture-Expanded Mesenchymal Stem Cells in the Microvasculature: In Vivo Observations of Cell Kinetics," *Circulation Research*, 2009, vol. 104, pp. 398-402.

Wall, M.E. et at., "Effects of Serial Passaging on the Adipogenic and Osteogenic Differentiation Potential of Adipose-Derived Human Mesenchymal Stem Cells," *Tissue Eng.*, 2007, vol. 13, No. 6, pp. 1291-1298.

Xian, C.J. and Foster, B.K. "Repair of injured Articular and Growth Plate Cartilage using Mesenchymal Stem Cells and Chondrogenic Gene Therapy," *Curr Stem Cell Res Ther*, 2006, vol. 1, pp. 213-229. (Abstract only).

Yang, Y., et al., "Ex Vivo Expansion of Rat Bone Marrow Mesenchymal Stromal Cells on Microcarrier Beads in Spin Culture," *Biomaterials*, 2007, vol. 28, pp. 3110-3120.

Zhang, M., et al., "SDF-1 Expression by Mesenchymal Stem Cells Results in Trophic Support of Cardiac Myocytes after Myocardial Infarction," *FASEB J.*, 2007, vol. 21, pp. 3197-3207.

Zhao, F. and MA, T. "Perfusion Bioreactor System for Human Mesenchymal Stem Cell Tissue Engineering: Dynamic Cell Seeding and Construct Development," *Biotechnol Bioeng*, 2005, vol. 91, No. 4, pp. 482-493.

Zhao, F., et al. "Effects of Shear Stress on 3-D Human Mesenchymal Stem Cell Construct Development in a Perfusion Bioreactor System: Experiments and Hydrodynamic Modeling," *Biotechnol Bioeng.*, 2007, vol. 96, pp. 584-595.

Zhao, F., et al., "Perfusion Affects the Tissue Developmental Patterns of Human Mesenchymal Stem Cells in 3D Scaffolds," *J. Cell. Physiol*, 2009, vol. 219, pp. 421-429.

Zhao, F., et al., "Effects of Oxygen Transport on 3-D Human Mesenchymal Stem Cell Metabolic Activity in Perfusion and Static Cultures: Experiments and Mathematical Model," *Biotechnology Progress*, 2005, vol. 21, pp. 1269-1280.

MESENCHYMAL STEM CELLS (MSC) EXPANSION METHODS AND MATERIALS

CROSS-REFERENCE TO RELATED APPLICATION

The present application claims the benefit of U.S. Provisional Application Ser. No. 61/421,889, filed Dec. 10, 2010, which is hereby incorporated by reference herein in its entirety, including any figures, tables, nucleic acid sequences, amino acid sequences, or drawings.

GOVERNMENT SUPPORT

This invention was made with government support under grant number W81XWH-07-1-0363 awarded by the Department of Defense. The government has certain rights in the invention.

BACKGROUND OF THE INVENTION

Introduction

Recently, human mesenchymal stem or stromal cells (hMSC) isolated from bone marrow or adipose tissue (hAMSC) (and increasingly from other tissue sources) have generated a wave of enthusiasm in both scientific and clinical communities because of therapeutic prospect for many devastating diseases (Prockop and Olson, 2007). Attractive properties of these reparative adult stem cells are that they can be readily isolated from a small tissue sample and expanded in culture and that they will home to injured tissue and enhance tissue repair (Salem and Thiemermann, 2010). To realize the potential of hMSC's in clinical applications, a significant challenge is to obtain them in sufficient quantity that they will have the required therapeutic potency (Prockop, 2009; Tang et al., 2007). Because of the low occurrence of MSC in vivo, only culture-expanded MSCs are likely to meet the demands of clinical use. Traditional cell-culture techniques facilitate billion-fold expansion of hMSCs, but result in a gradual loss of their self renewal and stem cell properties (Bruder et al., 1997). Such sequential passaging is also associated with a decrease in hMSC's responsiveness to stimuli at wound sites and reduction in their ability to secrete therapeutic factors, thus compromising the therapeutic outcome (Honczarenko et al., 2006; Son et al., 2006; Rombouts and Ploemacher, 2003). Recent studies have shown that the standard culture requires lengthy expansion to obtain sufficient quantity for transplantation, leads to genetic and epigenetic changes, and alters basic cell properties such as increasing of cell size with reduced cell mobility and therapeutic efficacy (Toma et al., 2009; Furlani et al., 2009; Lee et al., 2010; Rayment and Williams, 2010). Thus, a novel cell expansion strategy that supports robust hMSC proliferation without malignant transformation and senescence while preserving their multilineage and therapeutic potency is critical to overcome the limitation of conventional culture methods impeding hMSC's therapeutic applications.

In sharp contrast to the diminishing stem cell properties in vitro, hMSCs have remarkable in vivo self-renewal ability and multi-lineage potential over the life-time of an individual. Increasing evidence suggests that the specialized in vivo bone marrow microenvironment (ME) or niche supports MSC self-renewal and helps maintain their multi-potentiality, which are missing in the standard culture systems. The critical niche elements include extracellular matrix (ECM) proteins, growth factors (GFs), and surrounding cells. Biomechanical factors such as substrate rigidity as well as biochemical factors such as oxygen tension are also integral niche components and regulate stem cell behaviors (Discher et al., 2009). Considering the profound influence of the stem cell niche, recapitulating the cellular and structural components of the in vivo MSC ME has become an important approach to provide the cells with appropriate cues during expansion, thereby preserving the primitive stem cell properties. The success of the bio-inspired, engineered ME for ex vivo hMSC expansion ultimately depends on deciphering the roles of the ME components and their regulatory pathways and on successful synthesis of these multifaceted factors in an efficient and reproducible fashion.

MSC in Stem Cell Therapy.

Mesenchymal stem cells (MSC) isolated from bone marrow are among the most widely used stem cell types in cell therapy due to several favorable biological characteristics, including their convenient isolation from adult donors, ease of expansion while maintaining genetic stability (Bernardo et al., 2007), lack of immunogenicity and feasibility for allogenic transplantation (Aggarwal and Pittenger, 2005; Le Blanc et al., 2003), and horning to sites of tissue injury and repair the tissue, either by differentiating into tissue-specific cell phenotypes (Zhang et al., 2007; Barbash et al., 2003; Pereira et al., 1998; Ferrari et al., 1998; Liechty et al., 2000; Dezawa et al., 2001), or by creating a milieu that modulates the immune response (Chen et al., 2001; Hofstetter et al., 2002; Ankeny et al., 2004). Culture expanded MSCs have been approved for clinical trials for treatment of numerous ailments including hematopoietic diseases (Lazarus et al., 2005; Koc et al., 2000) cardiovascular diseases (Nagaya et al., 2005; Katritsis et al., 2005) brain and spinal cord injury (Sykova et al., 2006), cartilage and bone injury (Ohgushi et al., 1989; Xian and Foster, 2006; Quarto et al., 2001) and bone and cartilage regeneration (Sakai et al., 2006). While the use of hMSCs in the clinical arena has generated great excitement (there are more than 200 clinical trials are currently exploring the application of MSC as reported at http://clinicaltrials.gov), significant challenges must be overcome prior to the clinical application of hMSC. First, in the bone marrow obtained from human donors, hMSC's are rare and in the range of approximately 1 in $10^5$ nucleated cells (Bruder et al., 1997). While culture expansion is a necessary step to acquire sufficient quantities of cells for therapeutic application, culture-induced transformation is a significant barrier in stem cell-based therapy that impacts patient safety and therapeutic efficacy. hMSC in culture was shown to be associated with a diminishing proliferation rate and a gradual loss of multi-lineage differentiation capacity and their ability to respond to chemical stimuli (Kertlow et al., 2008; Wall et al., 2007; Banfi et al., 2000). Poor cell engraftment and migration, massive cell death and extreme low viability (<5%) post-transplantation have also been reported in the treatment of ischemic heart and brain injuries (Salem and Thiemermann, 2010; Mangi et al., 2003). Understanding hMSC behaviors in culture and developing novel strategies that promote hMSC proliferation while preserving their therapeutic potency are critically important.

Standard plastic culture-wares are typically used to expand hMSC for clinical studies, including hMSC transplantation to patients with stroke (Lee et al., 2010), acute myocardial infarction (Chen et al., 2004), and severe limb ischemia (Lasala et al., 2010). Based on current literature, conventional culture remains the prevailing method to expand hMSCs for transplantation and has been implicated for the limited success in hMSC's therapeutic applications (Prockop and Olson, 2007;

Salem and Thiemermann, 2010; Prockop, 2009; Tang et al., 2007; Lee et al., 2010; Prockop et al., 2010).

Studies have begun to reveal the adverse impact of the conventional culture method on hMSC properties, especially cell migration and survival. Sequential passaging of MSC using standard methods has been shown to be associated with a decrease in expression of adhesion molecules, the loss of chemokine receptors, enlargement of cell size, and lack of chemotactic response to chemokines, thus compromising their therapeutic potency. The culture-expanded MSCs were entrapped at the pre-capillary level because of their large size after intra-arterially delivery, leading to micro-ischemia and significant loss of cell population (Toma et al., 2009; Furlani et al., 2009). Freshly isolated murine MSCs have high efficiency for homing to bone marrow following infusion but lose their homing ability after culture expansion (Rombouts and Ploemacher, 2003). In stoke treatment, culture expanded hMSCs at passage 2 (P2) have significantly higher trophic factor secretion (e.g., VEGF, EPGF, BDNF, bFGF) as compared to those of P6 hMSCs, although both have similar morphologic features, viability, and tri-lineage differentiation capacity (Li et al., 2008). In addition, homing receptors such as CXCR4, a chemotactic receptor for SDF-1, is usually absent on the surface of culture-expanded MSCs (Karp and Teo, 2009; Sackstein et al., 2008). As a result, limited targeting capability of culture-expanded hMSC and very low graft survival rate require the delivery of a large number of cells to achieve the therapeutic effects. Because MSC's therapeutic value depends not only on multi-lineage potency but also homing and engrafting abilities, strategies are being actively sought to preserve their sternness and enhance their therapeutic potential (Kuhn and Tuan, 2010; Karp and Teo, 2009). A novel cell expansion approach that not only expands the cell population but also preserves surface markers and horning ability will play a pivotal role in these efforts.

The recognition that the standard culture methods are unphysiological and the need to supply hMSC in sufficient quantity have inspired the bioreactor development for MSC expansion. Micro-carrier suspension culture has been used to support MSC with comparable growth kinetics on tissue culture plastics with reduced apoptosis and improved osteogenic differentiation potential (Yang et al., 2007). Bone marrow derived cells have also been expanded in non-adherent stirred suspension culture (Baksh et al., 2007). Using a single-pass perfusion bioreactor, MSCs have also been expanded as an adherent cell layer on a 2D surface and clinical scale MSC expansion with osteogenic potential was achieved (Dennis et al., 2007; Marolt et al., 2010). While these bioreactors provide a controllable bulk growth environment, there is limited control over the microscopic cellular ME such as cell-cell and cell-material interactions, which is critical for preserving MSC properties during expansion. In addition, the biomechanical forces induced in the suspension culture system may function as a selective force on the heterogeneous MSC population and impact MSC properties and its immediate ME. We have shown that media flow even at the lower end of the physiological range can significantly bias the distribution of regulatory macromolecules due to their low diffusivity, thereby influencing the cellular outcomes (Zhao et al., 2007). Thus, the need to control the bulk macro-environmental parameters in a bioreactor system must be balanced against the needs to optimize local interactions between cells and local cellular and physiochemical ME interactions to achieve sustained MSC expansion.

hMSC ME Formation and Regulation.

hMSCs, the stromal cells in the bone marrow, are responsible for the formation of the in vivo ME that includes soluble factors and an ECM network. The extracellular signals generated by the surrounding ME, such as cell-cell interactions, secreted and ECM-bonded GFs, molecules of ECM, and local physiological environments, work in intricate harmony to influence MSC identify and regenerative abilities. The ECM not only mediates cell adhesion but also binds GFs and so influences their spatial presentation to the cells. The functional secretions of bioactive factors are important characteristics of MSC. In fact, MSC's therapeutic potency has been attributed to the secreted bioactive factors that suppress the local immune system, inhibit apoptosis, enhance angiogenesis, and stimulate mitosis and tissue-specific differentiation (Caplan and Dennis, 2006). Referred to as trophic effects, the secreted factors have effects on cells in their vicinity either directly or indirectly, constituting an important component of the stem cell ME. Marrow ECM as well as the ECM made by cultured MSC profoundly influence MSC behaviors, from proliferation to lineage-specific differentiation and apoptosis (Chen et al., 2007; Klein, 1995). Thus, it is important to recapitulate the multifaceted niche factors as well as their dynamic interplay if any desired stem cell response is to be made robust for cell therapy.

In addition to the biological factors, one developmentally important stimulus that is still rarely accounted for during in vitro stem cell expansion is the $O_2$ tension. Although the role of $O_2$ as a metabolic substrate has been investigated extensively for cell expansion, much less studied has been the utilization of oxygen as a signaling molecule to influence stem cell behavior in culture. (In the subject application, $O_2$ levels lower than 20% are termed hypoxic and 20% $O_2$, normoxic, for consistency with conventional terminology.) In general, MSCs exhibited greater colony-forming potential (Grayson et al., 2006; Lennon et al., 2001) proliferated longer (Grayson et al., 2007; Fehrer et al., 2007; Buravkova and Anokhina, 2007), and maintained their undifferentiated characteristics better under hypoxia conditions (D'Ippolito et al., 2006). Hypoxia is also a potent inducer for the secretion of angiogenic factors by MSCs, contributing to the therapeutic benefits (Potier et al., 2007; Sadat et al., 2007; Gnecchi et al., 2006). Hypoxia inducible factors (HIFs) are the central regulator and mediate MSC' defining features including self-renewal and multipotency in response to a low oxygen environment (Keith and Simon, 2007). Given hypoxia's essential role in hMSC behaviors, incorporating optimal oxygen conditions in the culture system can reproduce the physiological conditions (as low as 1-2% (Kofoed et al., 1985)) that contribute to adult stem cells' remarkable feat of self-renewal and the maintenance of multi-potency through adulthood. However, in contrast to the increasing knowledge of hypoxia effects on cell cycle and proliferation, the effects of oxygen tension on the macromolecular milieu of hMSC ME and its subsequent influence on hMSC properties have not been effectively incorporated in the hMSC culture expansion systems.

BRIEF SUMMARY OF THE INVENTION

The subject invention concerns materials and methods for growing and expanding stem cells while maintaining their undifferentiated phenotype, self-renewal ability, therapeutic potency, and/or multi-lineage potential. In one embodiment, a method of the invention comprises i) seeding freshly isolated MSC on a planar surface or a porous 3-D scaffold and growing the cells under physiological or low $O_2$ tension (e.g., lower than 20% $O_2$) for a period of time sufficient to support formation of 3-D ECM network; ii) decellularizing the planar surface or 3-D scaffold; and iii) reseeding the decellularized planar surface or 3-D scaffold with MSCs, whereby the reseeded MSCs grow on the scaffold and maintain an undifferentiated phenotype. In a specific embodiment, the 3-D scaffold comprises or is composed of non-degradable polymer such as poly(ethylene terephthalate) (PET).

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 3A-1, 3A-2, 3A-3, 3A-4, 3B, 3C-1, 3C-2, and 3D. Human MSC growth and morphologies under hypoxia or normoxia on three different surfaces, such as tissue culture plate (TP), M(N), and M(H). (FIGS. 3A-1, 3A-2, 3A-3, and 3A-4). hMSC growth on TP, M(N), and M(H) under hypoxia or normoxia. The cell numbers were higher on both M(N) and M(H) compared with ones on TP. Hypoxia further increased cell numbers on all conditions. (FIG. 3B). The morphologies were changed dramatically between on TP and on ECM matrices. Cell size was smaller on M(N) and M(H) compared with one on TP. Values are means±SD for three samples of each condition (*:$P<0.05$, **:$P<0.01$). (FIGS. 3C-1 and 3C-2). Colony forming unit-fibroblast (CFU-F). (FIG. 3D). Crystal violet staining for counting colony numbers. Colony sizes on M(N) and M(H) were much bigger than ones on TP. In addition, colony numbers on M(N) and M(H) were significantly higher than ones on TP. Hypoxia further maintained colony numbers compared with normoxia. Values are means±SD for three samples of each condition (*:$P<0.05$, **:$P<0.01$). M(N)=matrix prepared with cells grown under normoxia condition. TP=tissue culture plate. M(H)=matrix prepared with cells grown under hypoxic conditions.

FIG. 4A shows staining for FN component. FIG. 4B shows staining for LN component. FIG. 4C shows staining for VN component. FIG. 4D shows staining for COL I component. FIG. 4E shows staining for COL III component. FIG. 4F shows staining for COL IV component. The decellularized ECM matrices maintained their structure after cell removal. Magnification, ×200. FN=fibronectin; LN=laminin; VN=vitronectin; COL I=collagen I; COL III=collagen III; COL IV=collagen IV.

DETAILED DESCRIPTION OF THE INVENTION

Figure 1:
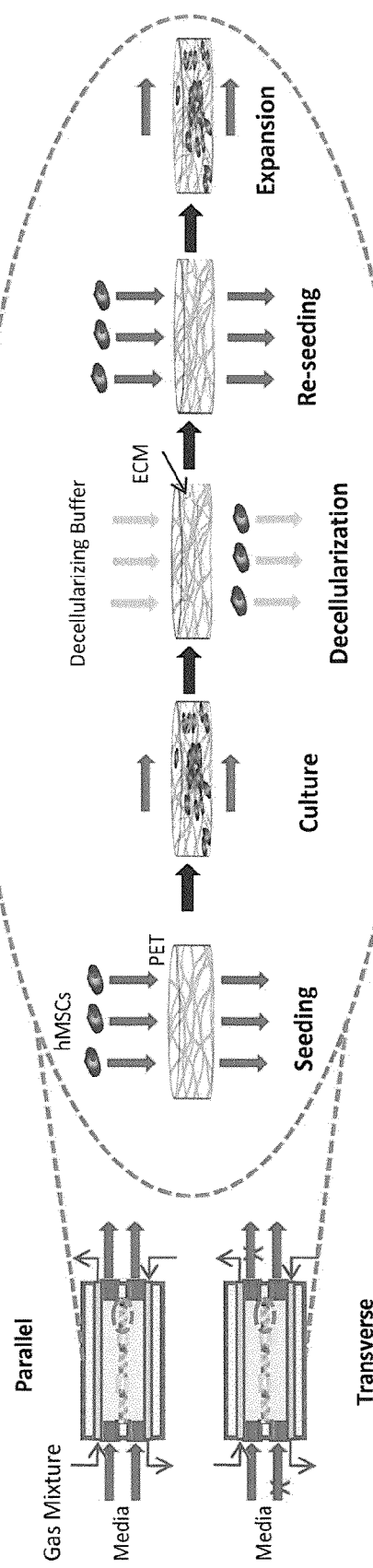
FIG. 1 shows an example of a process of the invention using a perfusion bioreactor for a streamlined hMSC ex vivo expansion process. Flow in the chamber can be controlled in either parallel (PF) or transverse (TF) to the scaffold, while $O_2$ tension is controlled by the gas mixture in the gas pouches. TF can be used for seeding and decellularization and PF for culturing. Following decellularization, freshly isolated hMSCs can be re-seeded by TF and then cultured for long-term expansion.

The subject invention concerns materials and methods for growing and expanding mammalian MSC while maintaining their undifferentiated phenotype, self-renewal ability, and/or multi-lineage potential. In one embodiment, a method of the invention comprises i) seeding freshly isolated MSC on a planar surface, such as plastic tissue culture plates, or on a 3-D scaffold and growing the cells under physiological or low $O_2$ tension (e.g., lower than 20% $O_2$) for a period of time sufficient to support formation of 3-D ECM network; ii) decellularizing the cultures on the plates or the 3-D scaffold to obtain decellularized ECM matrices thereon; and iii) reseeding the decellularized matrices on the plates or 3-D scaffold with MSCs, whereby the reseeded MSCs grow on the plate or scaffold that comprises cell-derived 3-D ECM and maintain an undifferentiated phenotype. The reseeded MSCs can also be grown on the culture plates or 3-D scaffold under physiological or low $O_2$ tension. In one embodiment, the MSC cells can be grown on the planar surface or 3-D scaffold in media with low concentration (generally less than about 5% v/v) of animal serum (e.g., fetal bovine serum, human serum, etc.) or in serum-free media. In one embodiment, the reseeded MSC cultures are treated to detach the MSC and then the clusters of MSC and ECM matrices are transferred to a spinner flash and cultured in suspension. In one embodiment where a culture plate or scaffold comprises thermally responsive film or coating, the plate or scaffold is placed at room temperature or lower than room temperature (e.g., 4° C.) for a period of time (e.g., for about 1, 2, 3, 4, or more hours) and the cells are released as clusters and then transferred to a spinner flask. The cell clusters can then be cultured in suspension in the spinner flask. In one embodiment, the MSC are grown in the spinner flask under physiological or low $O_2$ tension.

In one embodiment, the MSC are grown on the planar surface or 3-D scaffold wherein the $O_2$ tension is maintained at between about 1% and 10%. In a specific embodiment, the $O_2$ tension is maintained at between about 1% and 5%. In a more specific embodiment, the $O_2$ tension is maintained at between about 1% and 3% (e.g., $O_2$ tension could be about 1%, 2%, or 3%).

In one embodiment, the planar or scaffold surface is one that has a thermoresponsive film that allows for cell detachment from the surface by modulating the temperature. Examples of thermoresponsive films include N-isopropylacrylamide, poly(allylamine hydrochloride)-co-poly(N-isopropylacrylamide), and poly(styrene sulfonate)-co-poly(N-isopropylacrylamide), and are described in Liao et al. (2010). In one embodiment, the surface comprises multiple layers of one or more thermoresponsive films. The thermoresponsive films can optionally comprise a terminal coating of a layer of positively charged allylamine hydrochloride (PAH), or negatively charged styrene sulfonic acid (PSS), or serum, such as fetal bovine serum (FBS).

In a specific embodiment, decellularization is performed using a detergent (e.g., Triton-X) and an enzyme that degrades nucleic acids (e.g., a DNase). Any suitable method for decellularizing the plate or 3-D scaffold is contemplated for use in the subject invention. In a specific embodiment, prior to decellularization, the MSC on the plate or 3-D scaffold are washed (e.g., with phosphate buffered saline (PBS)).

Expanded MSCs can be harvested following reseeding and growth of MSC. In one embodiment, MSC can be harvested up to 3 months following reseeding. In a specific embodiment, the MSCs used in the subject methods are human MSC (hMSC). In one embodiment, MSC for use in the invention can be isolated from bone marrow and/or adipose tissue of a mammal or human. In one embodiment, the MSC population obtained following the expansion of the reseeded cells exhibits enhanced Akt and/or ERK1/2 activity.

Figures 1, 3A:
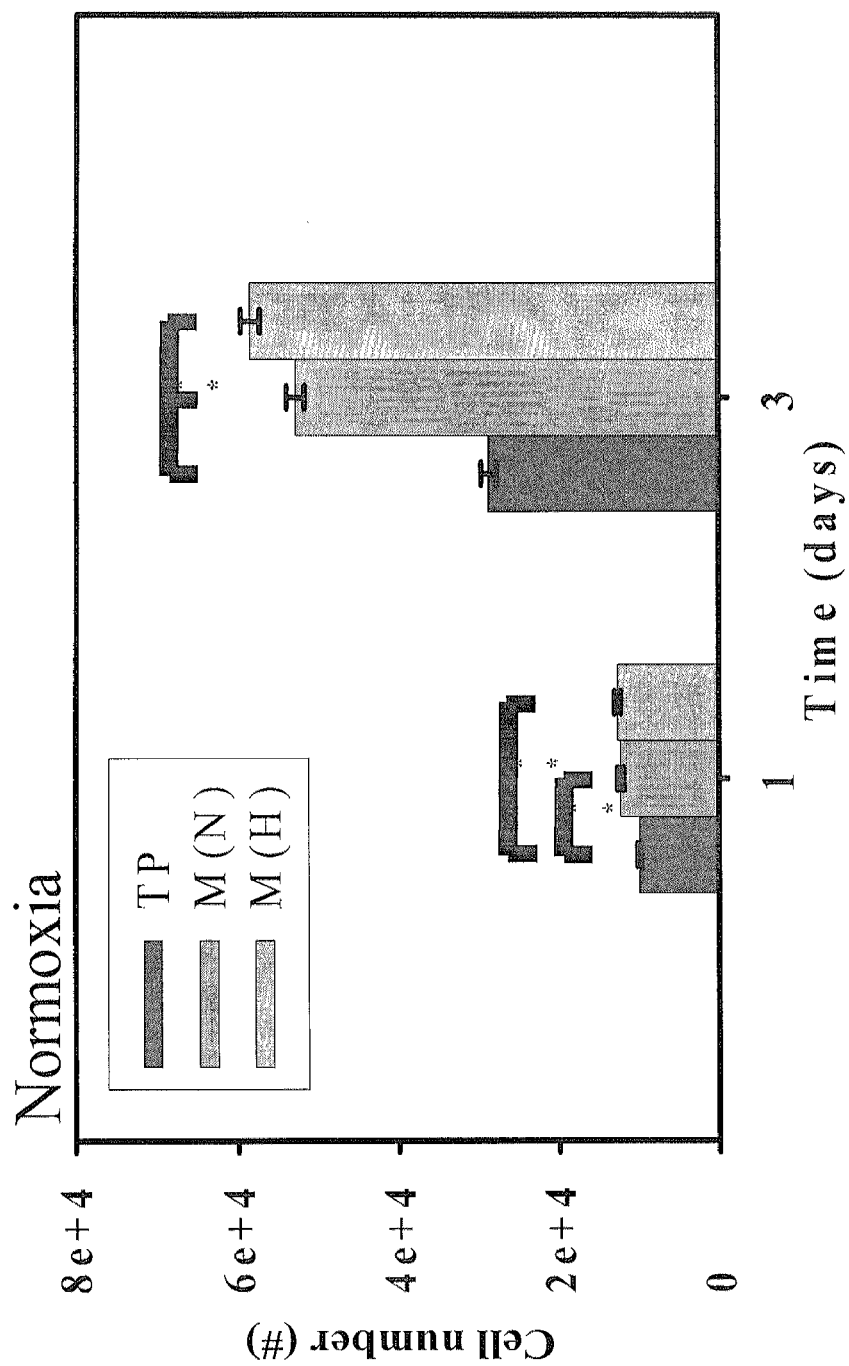
Figures 2, 3A:
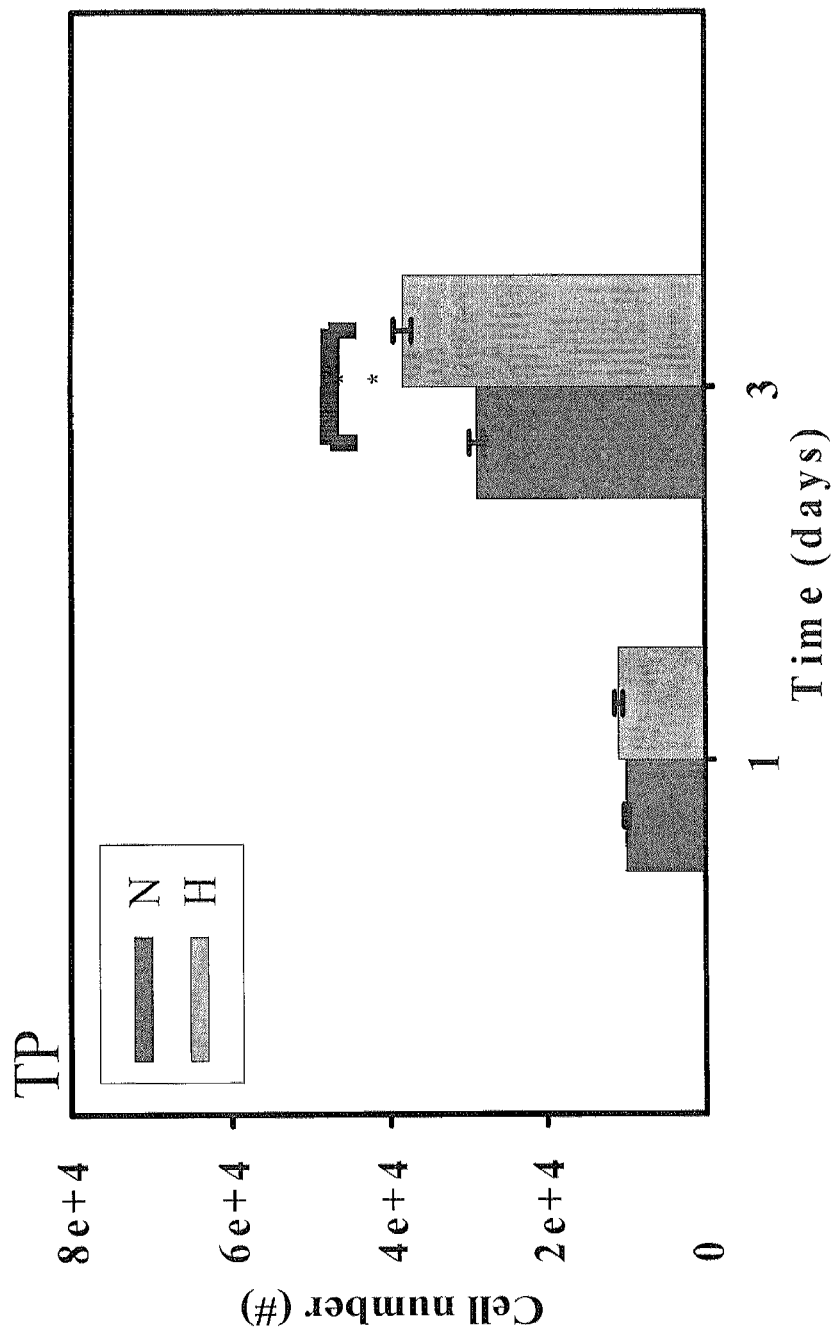
Figures 3, 3A:
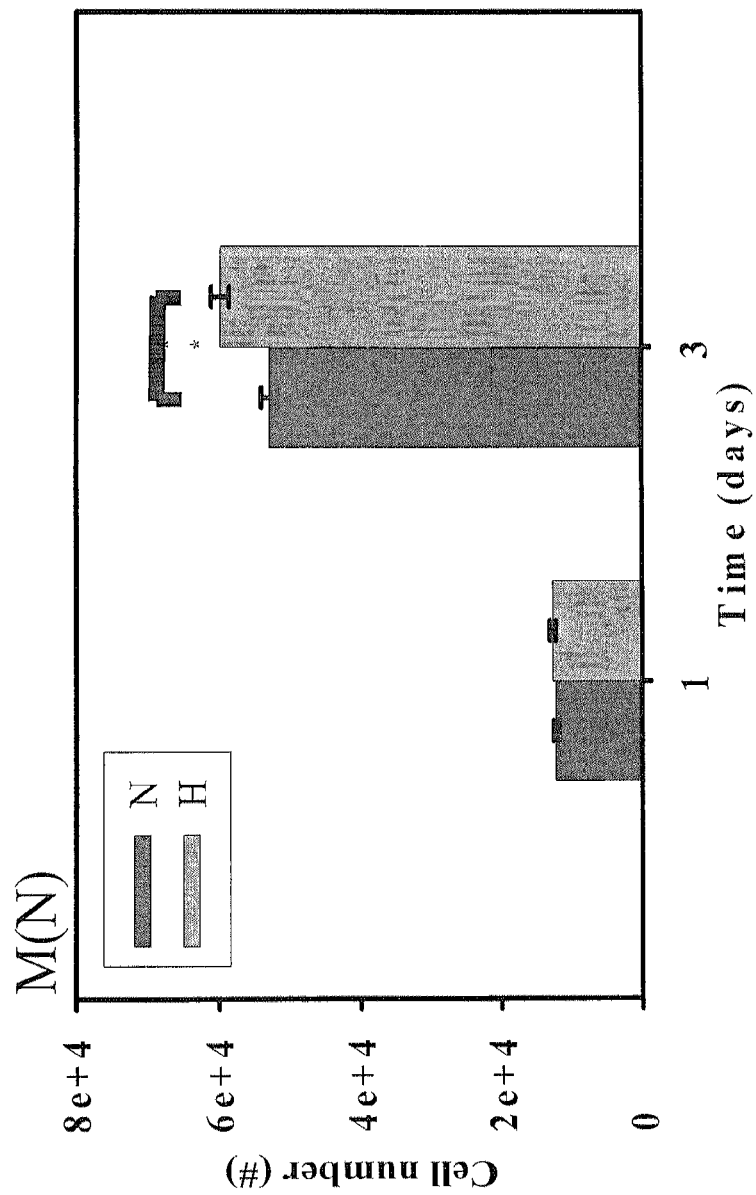
Figures 3, 3A, 4:
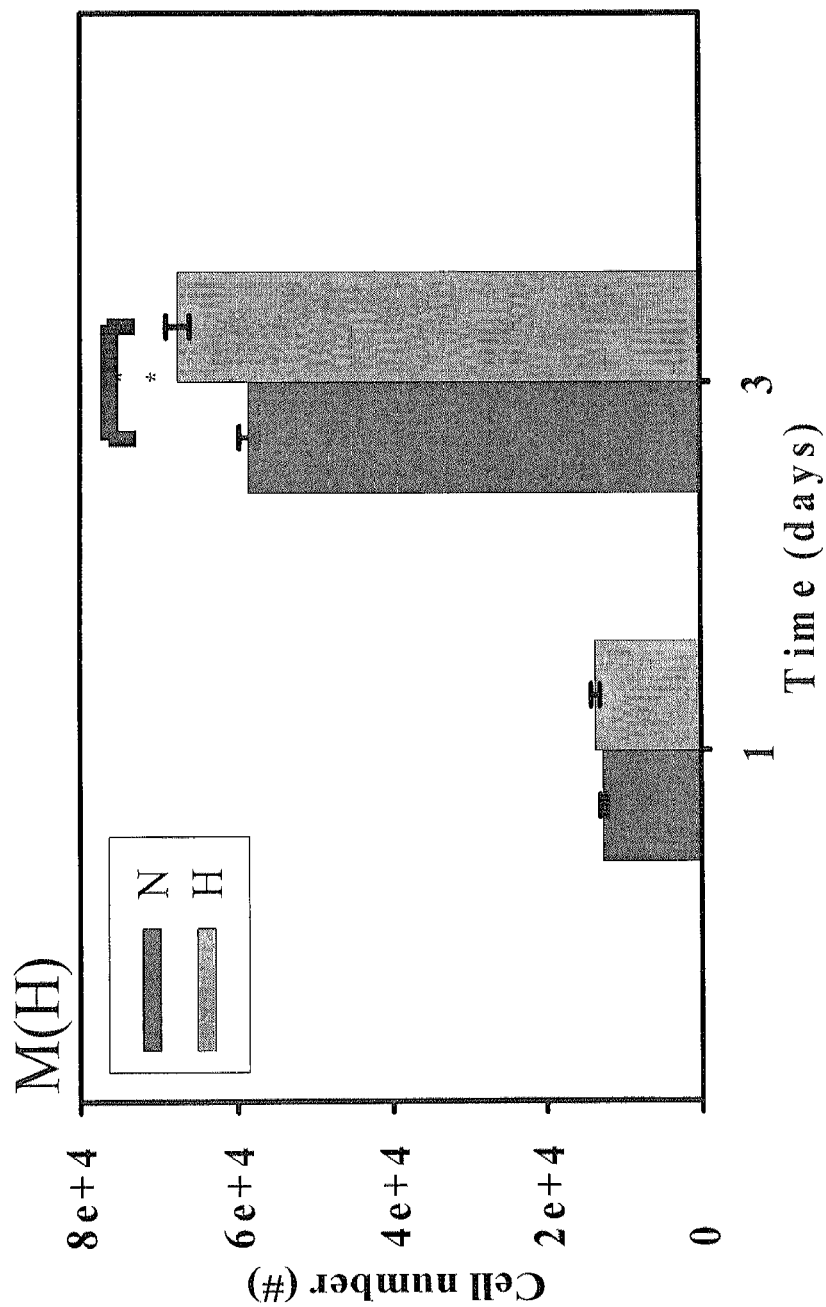
Figure 3B:
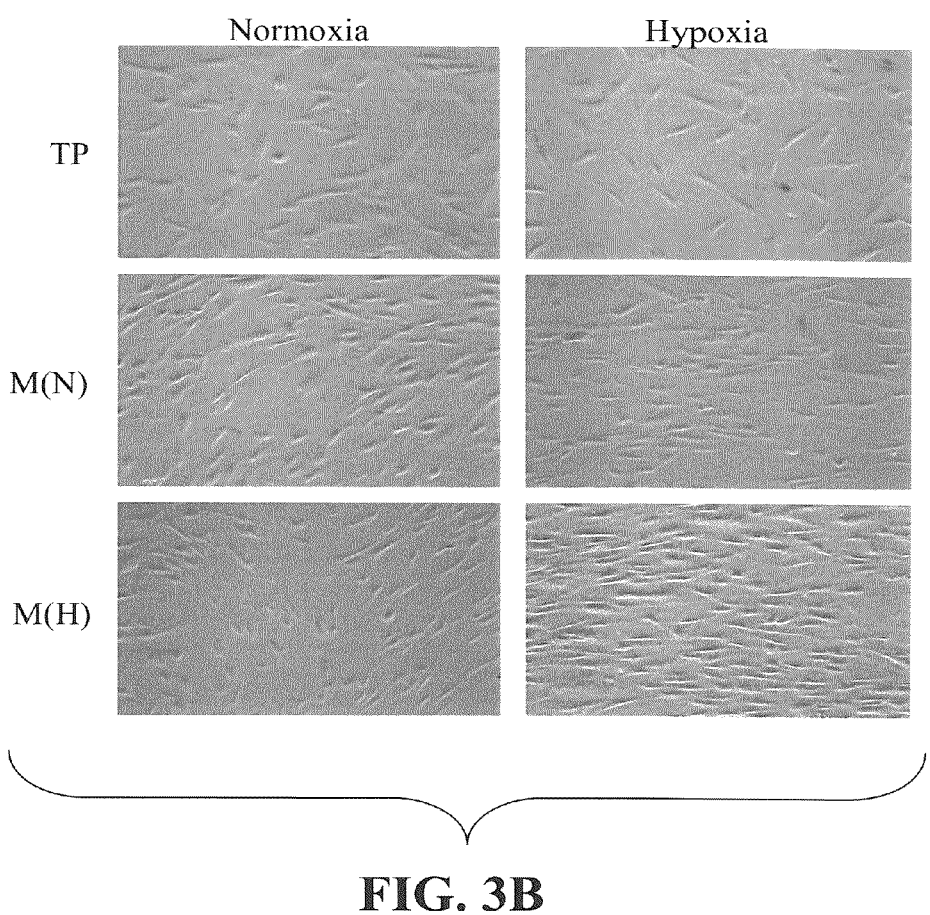
Figures 1, 3C:
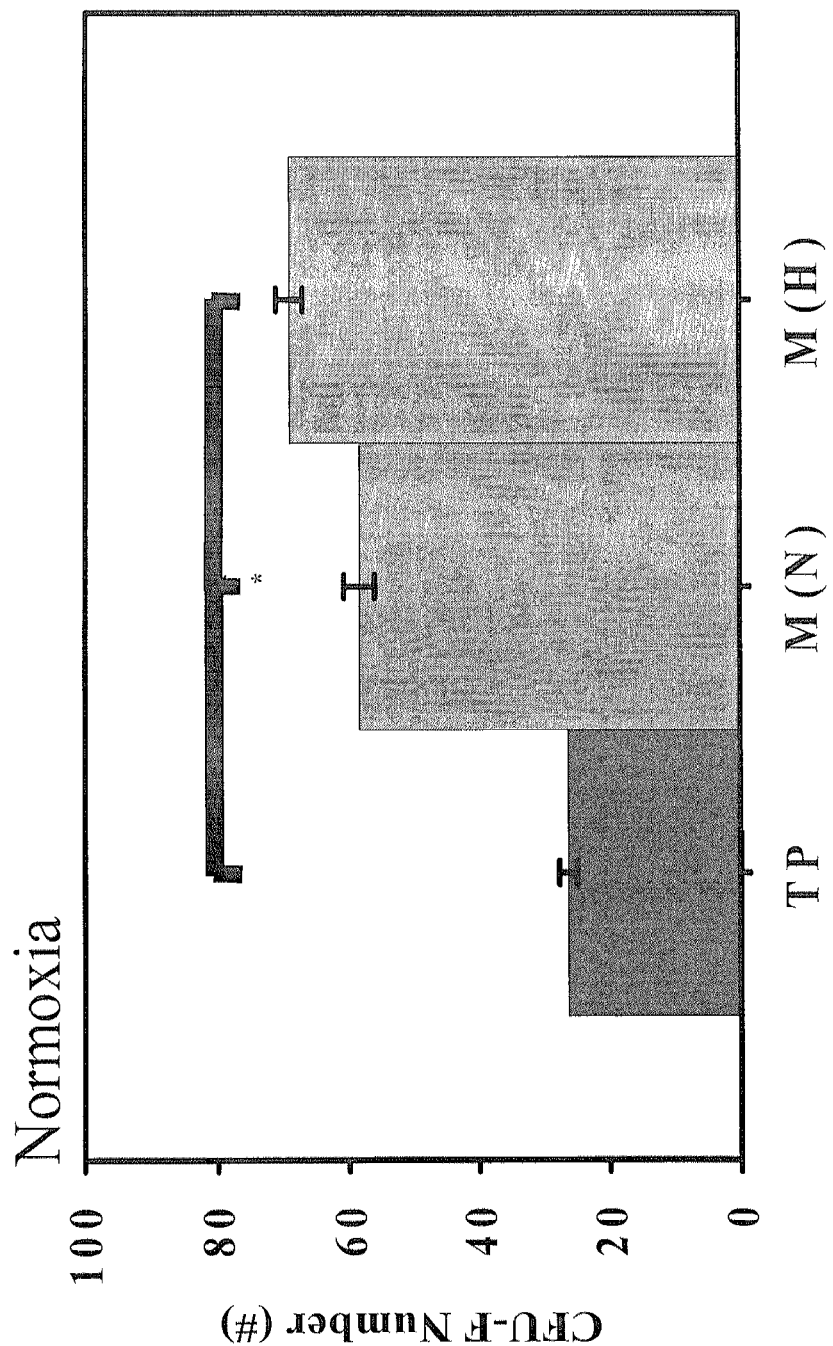
Figures 2, 3C:
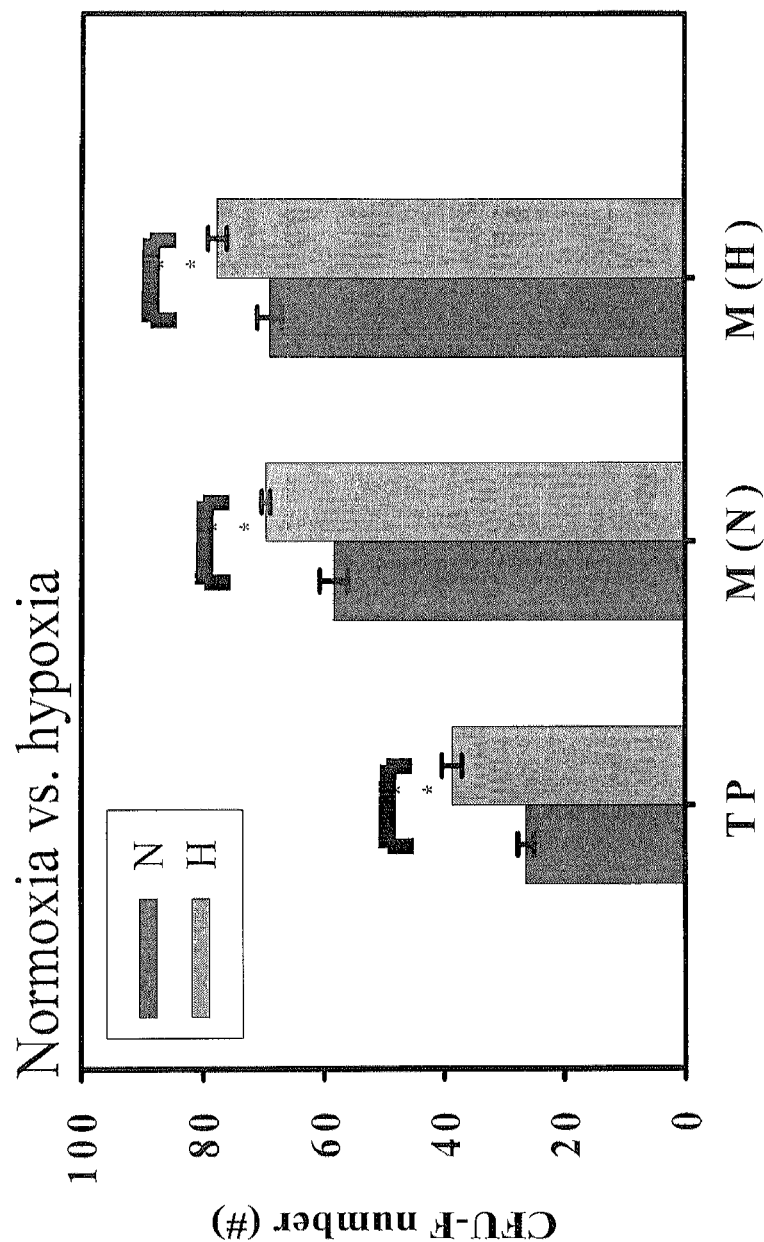
Figure 3D:
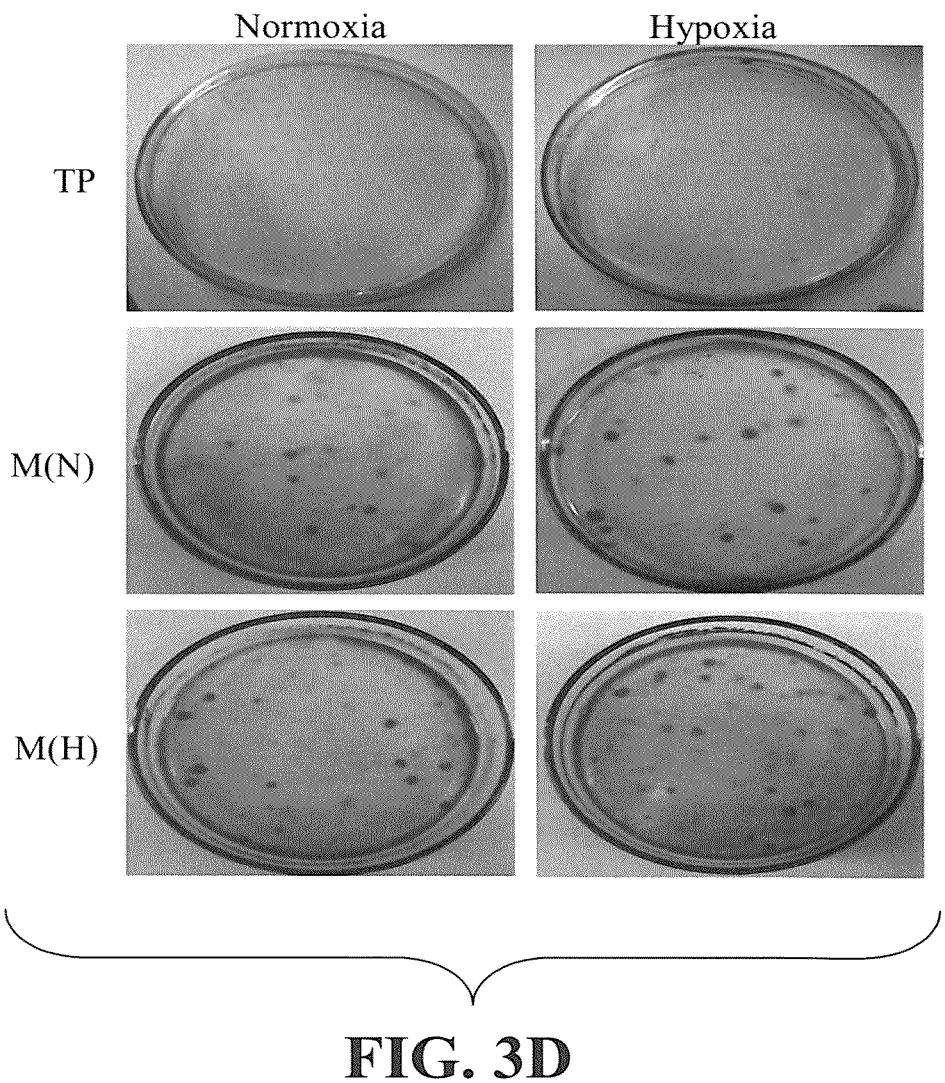
Figure 4A:
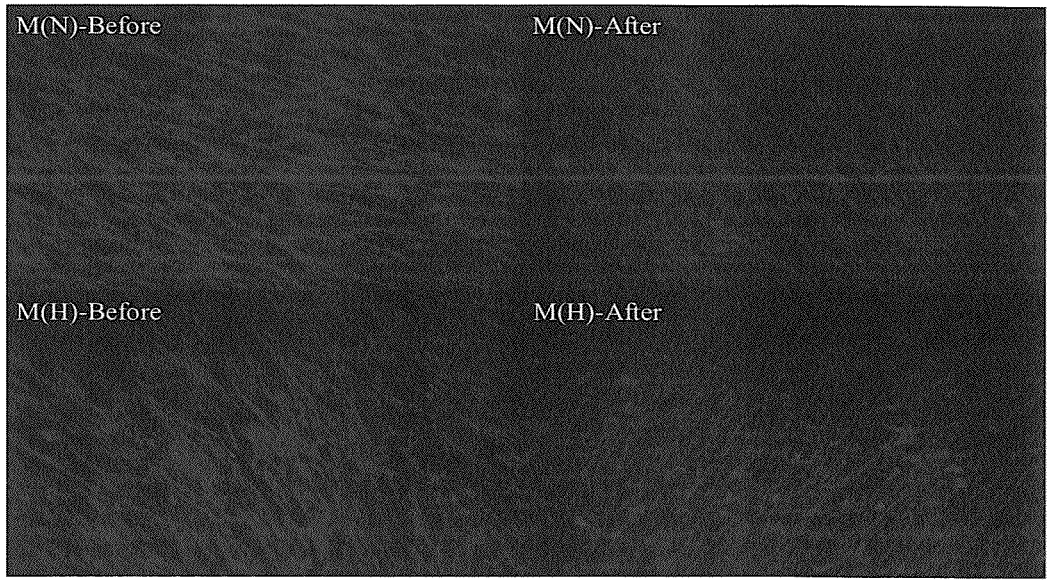
FIGS. 4A-4F show components of hMSC-derived ECM visualized by immunostaining before and after cell removal. Blue represents cell nuclei and green represents ECM component.
Figure 4B:
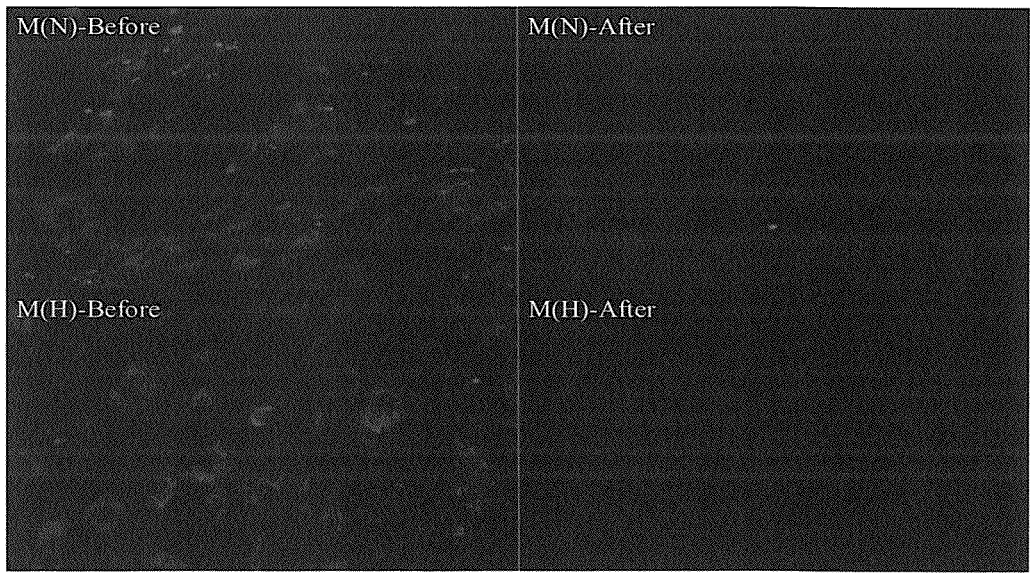
Figure 4C:
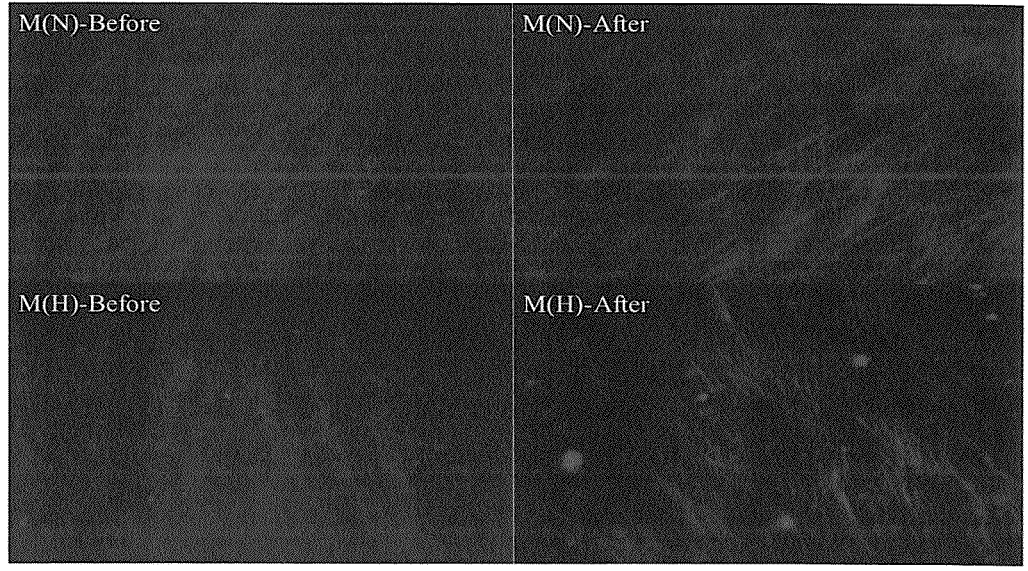
Figure 4D:
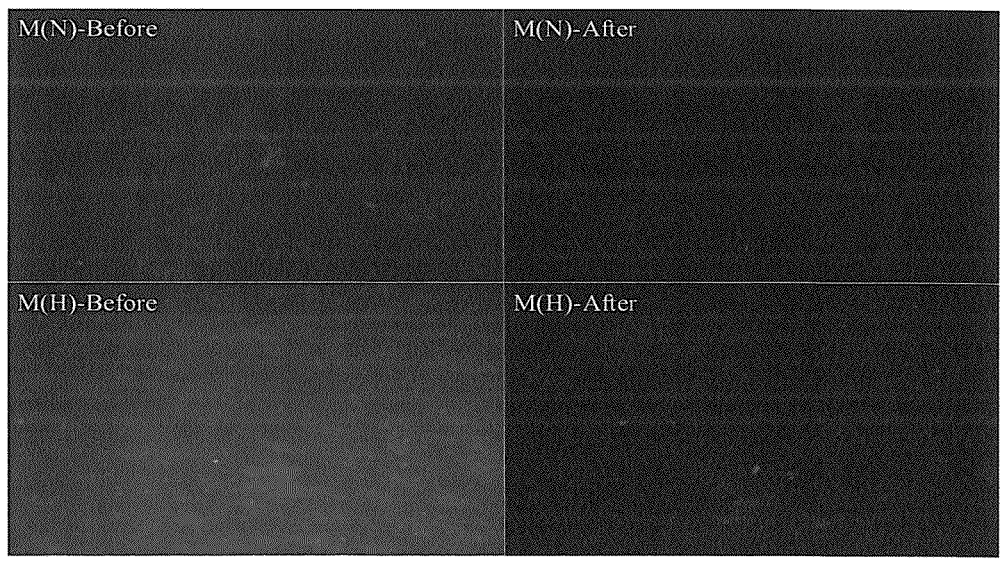
Figure 4E:
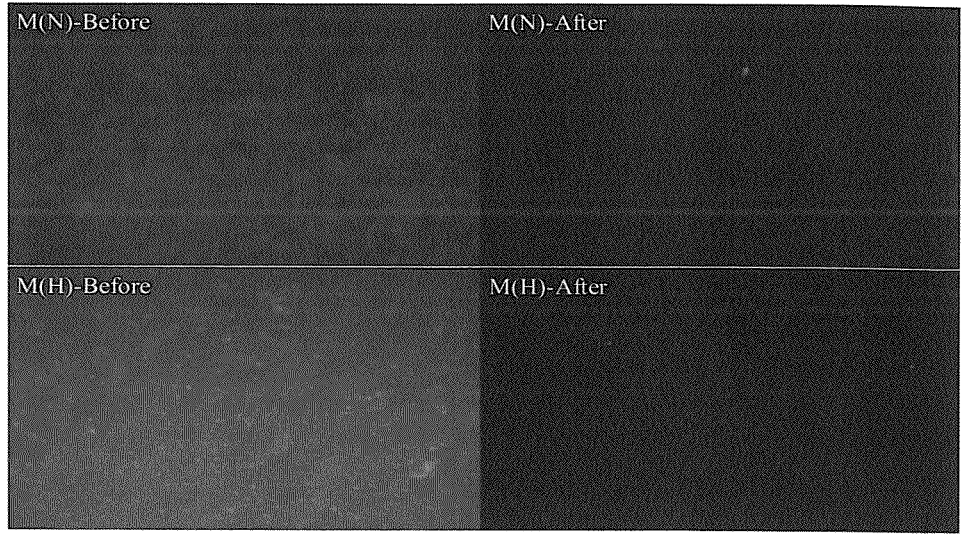
Figure 4F:
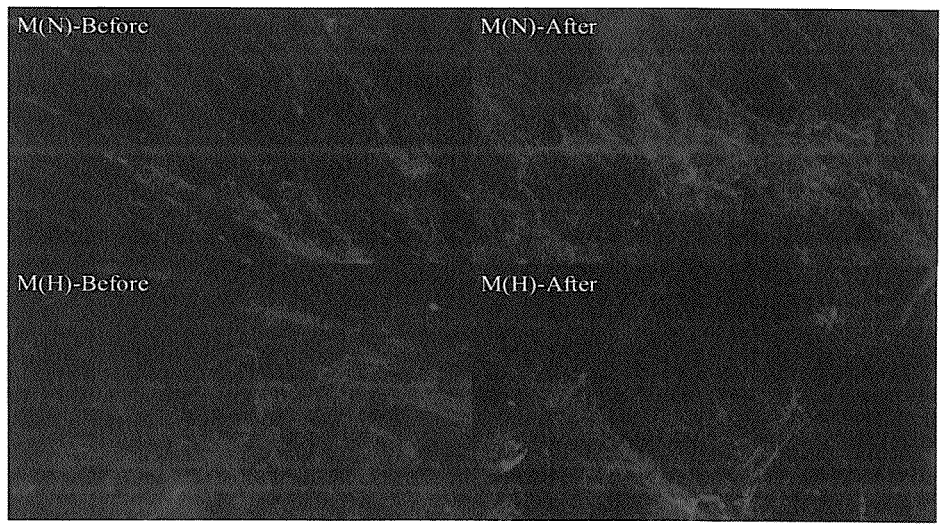
Figure 5:
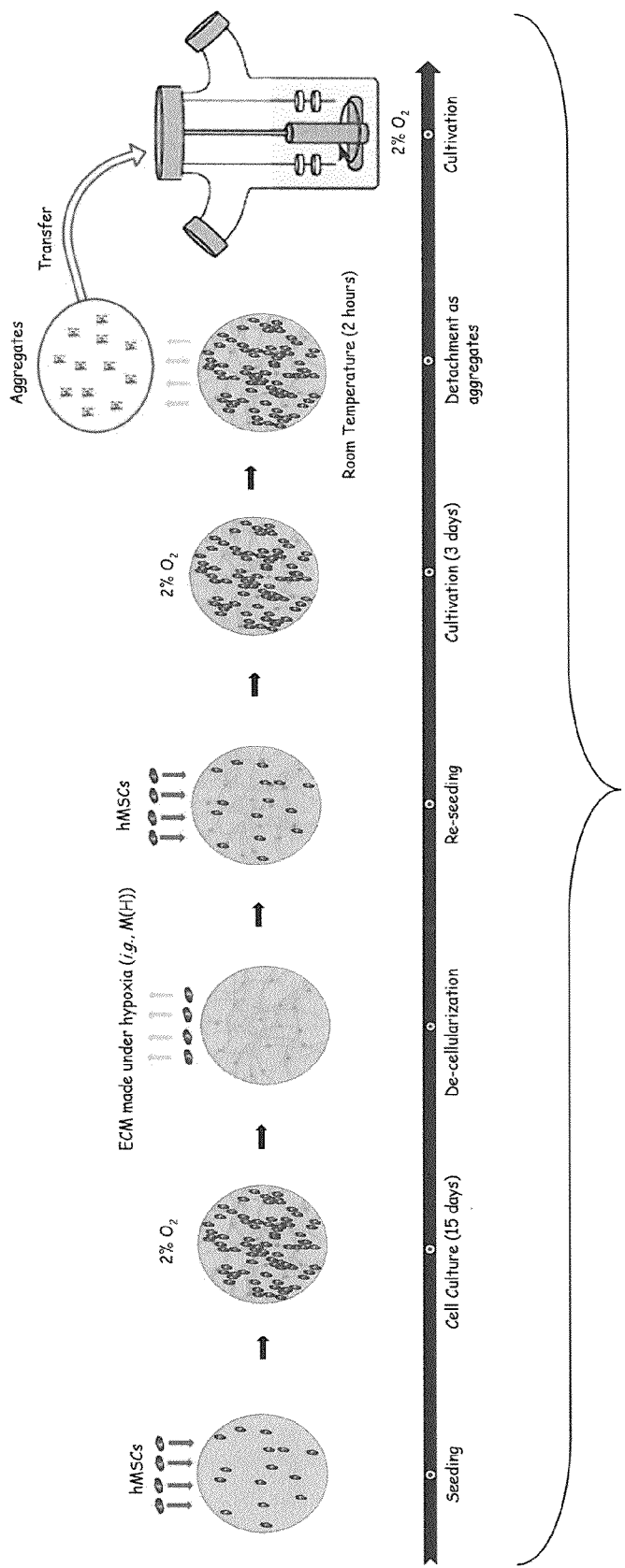
FIG. 5 shows an example of a process of the invention using tissue culture plates and spinner flask for ex vivo expansion of MSC.

The methods of the present invention provide for more rapid expansion of MSC population than conventional methods while preserving their native properties. ECM prepared under hypoxic (i.e., 2% $O_2$) and normoxic conditions were used in a colony forming unit-fibroblast (CFU-F) assay as described (Grayson et al., 2006) as shown in FIG. 3. Cells seeded on M(H) and grown under hypoxic conditions significantly increased CFU-F formation as compared to cells seeded on M(H) and grown under normoxic conditions or cells seeded on M(N) and grown under hypoxic conditions. In clinical applications, shortening the time required for autologous cell expansion is critical for transplantation. The subject invention also better maintains their survival and preserves the secretion of the therapeutic factors and thus their therapeutic potency compared to traditional culture methods. In addition, the methods of the subject invention utilize a lower serum concentration or patient-specific plasma than traditional culture methods. The presence of ECM matrices also better preserves hMSC viability and enhances their proliferation in serum-free media. The ability to use plasma from a patient can reduce the risk associated with exogenous proteins, such as serum proteins.

The 3D decellularized matrices can be constructed on planar surfaces, such as glass or plastic tissue culture plates (e.g., polystyrene), or in 3-D non-degradable scaffolds that are suitable for cell culture. The planar culture surfaces contemplated within the scope of the invention include those having a thermal responsive surface that release a cell and/or cell sheet at reduced temperature without enzymatic treatment. The 3D scaffolds of the invention include but are not limited to poly(styrene), poly(carprolactone), and nylon scaffolds. In a specific embodiment, the 3-D scaffold of the invention comprises or is composed of poly(ethylene terephthalate) (PET). In one embodiment, the MSCs are grown on the 3-D scaffold in a perfusion bioreactor. One embodiment of the subject invention is shown in FIG. 1. The PET scaffolds can have an isotropic fibrous structure with a porosity of about ~90%, an average pore diameter of 50-100 µm, and a fiber diameter of 20 µm. As shown in FIG. 1, three disks of PET scaffolds (diameter: 1.6 cm; thickness: 1.2 mm) are placed in the center of the perfusion chambers (width: 2.0 cm; length: 6.0 cm), partitioning the chamber into two identical compartments and allowing media flow either parallel or transverse to the scaffolds. The ability to modulate macroscopic flow in the perfusion chambers is an important feature of the perfusion bioreactor system described in U.S. Pat. Nos. 6,875,605 and 6,943,008 and Zhao et al. (2005), and is uniquely suited to achieve the automated cell seeding, decellularization, re-seeding of the freshly isolated MSC, and final cell harvesting in a single unit. The controlled convective flow in the perfusion chamber not only improves spatial cell distribution during seeding and re-seeding, but will also improve decellularization efficiency. The outcome of this is a novel, streamlined bioreactor-based cell expansion process that supports clinical scale MSC expansion.

PET is one of the earliest biomaterials approved as implantable materials for medical uses (Homsy et al., 1968; Klinge et al., 1998; Soares et al., 1996; Vinard et al., 1988; Riepe et al., 1997; Illingworth et al., 1998; Tweden et al., 1997). Non-woven PET scaffolds have excellent chemical and mechanical stability, and have been used as scaffolds to support the expansion of human hematopoietic stem cells and high density hMSC growth in the perfusion bioreactor (Grayson et al., 2004; Zhao and Ma, 2005; Zhao et al., 2007; Li et al., 2001). PET scaffolds' excellent biocompatibility and highly porous structure are ideal and an extensive ECM network can be formed and maintained in a structurally stable environment.

Figure 2:
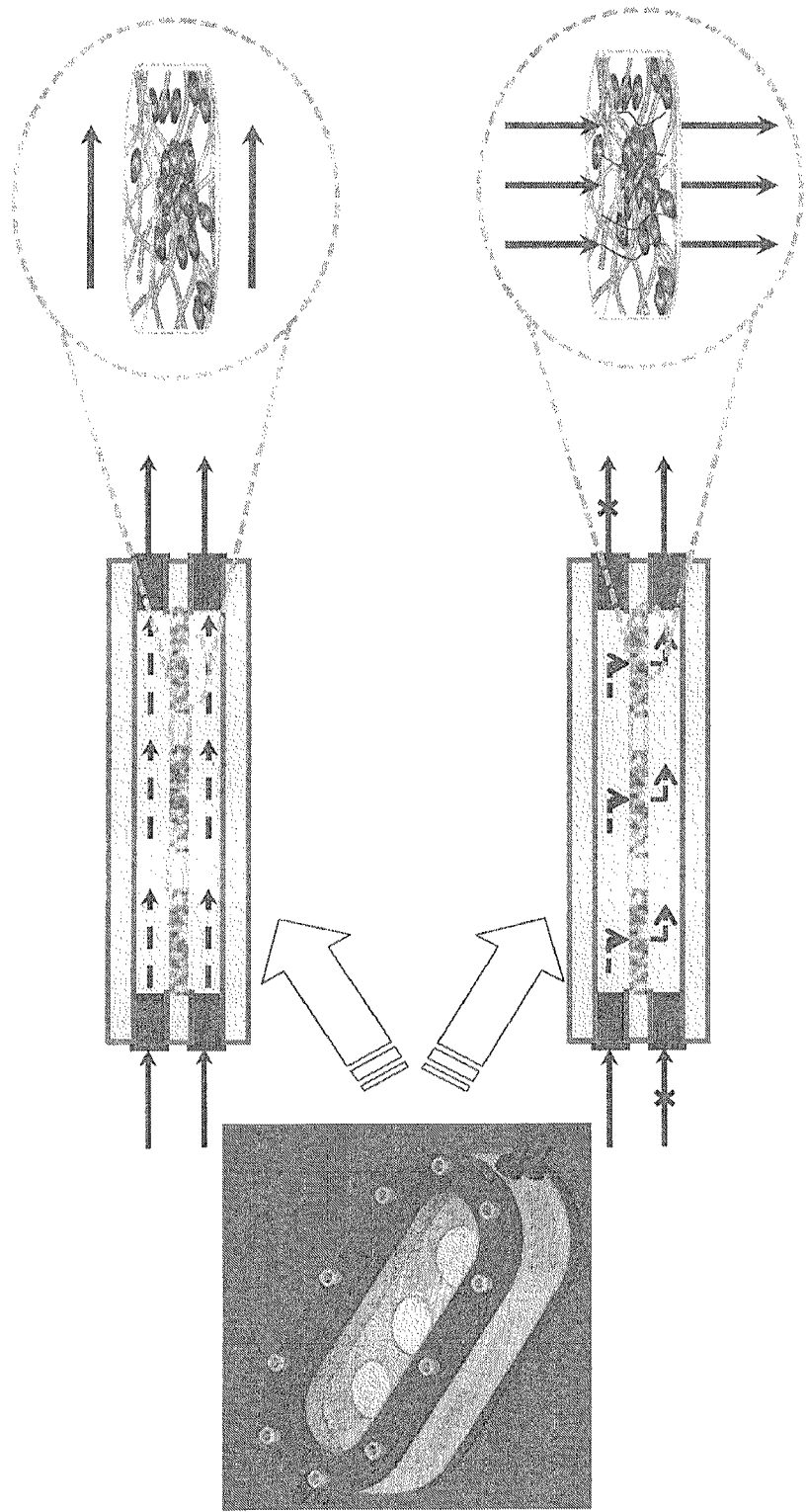
FIG. 2 shows an example of a perfusion bioreactor system that can be used in accordance with the present invention. The system features modular perfusion chambers with multiple sampling ports and has the capability for each chamber to be controlled individually and set for transverse (top) or parallel (bottom) flow, however, all chambers share the same media source and inoculum, facilitating comparison of various operating conditions (Zhao and Ma, 2005; Zhao et al., 2007).

A perfusion bioreactor device of the invention can be used to grow cells and tissue in a controlled in vitro environment (see, for example, FIG. 2). Perfusion bioreactor devices that can be utilized with the present invention include those described in U.S. Pat. Nos. 6,875,605 and 6,943,008. In one embodiment, a perfusion bioreactor device of the invention can have multiple perfusion chambers that can be controlled individually. Transverse or parallel flow of a fluid can be provided to each chamber. The fluid is one that is capable of providing appropriate conditions for cell life and/or supporting and directing growth and/or differentiation of cells within the device. For example, the fluid can be a fluid containing nutrients and other chemicals or factors, such as cytokines, to support the growth and/or differentiation of cells. In one embodiment, the perfusion bioreactor chamber has two or more compartments connected by a porous scaffold (onto which cells can be seeded), and conditions such as substance concentration, pressure, and fluid flow rate can be individually controlled in each compartment. The pressure in each chamber can be regulated so that the fluid can penetrate the scaffold transversely or horizontally on demand. The porous scaffold in the chamber supports cell growth and fluid penetration thereby providing space for the cells to form a functional tissue such as bone, cartilage, or tendon. In one embodiment, the porous scaffold is a porous hydrogel and/or 3D scaffold to provide a 3D environment in the bioreactor device where the cells can adhere, proliferate, migrate, secrete growth and/or differentiation factors, and/or undergo differentiation, etc. In one embodiment, a hydrogel and/or 3D scaffold comprises PET. The hydrogel or scaffold can optionally be provided in a shape that mimics or is similar to the shape of the tissue that is to be repaired or replaced in a human or animal. In addition, the pore size of the hydrogel or scaffold can be controlled and selected to promote growth of cells.

The subject invention also concerns isolated mammalian MSC that exhibit undifferentiated phenotype, self-renewal ability, and/or multi-lineage potential that have been produced using a method of the present invention. In a specific embodiment, the MSC are human MSC. The isolated MSC can be used to treat disease in a human or animal, and to repair injured tissue. In one embodiment, the MSC exhibit enhanced Akt activity and/or ERK1/2 activity.

The subject invention also concerns a planar surface or a 3-D scaffolds that have been prepared by seeding freshly isolated MSC on a planar surface or 3-D scaffold and growing the cells under physiological or low $O_2$ tension as described herein and for a period of time sufficient to support formation of a 3-D ECM network, followed by decellularizing the planar surface or 3-D scaffold as described herein. The prepared planar surface or 3-D scaffold can then be used to grow and expand MSC that are reseeded on the planar surface or 3-D scaffold. The subject invention also concerns a planar surface or 3-D scaffolds that have the reseeded and expanded MSC thereon that exhibit an undifferentiated phenotype, self-renewal ability, and/or multi-lineage potential. In one embodiment, the scaffold is in a shape that mimics the shape of a tissue to be repaired or replaced. In a specific embodiment, the 3-D scaffold comprises PET. In one embodiment, the MSC are grown on the 3-D scaffold in a perfusion bioreactor.

An example of a claimed embodiment of the invention is shown below:

A method comprising i) seeding freshly isolated MSC on a 3-D scaffold and growing the cells under physiological or low $O_2$ tension (e.g., lower than 20% $O_2$) for a period of time sufficient to support formation of 3-D ECM network; ii) decellularizing the 3-D scaffold; and iii) reseeding the decellularized 3-D scaffold with MSCs, whereby the reseeded MSCs grow on the scaffold that comprises cell-derived 3-D ECM and maintain an undifferentiated phenotype.

Materials and Methods hMSCs.

Commercially available adult human bone marrow-derived MSCs are used in the study. For normoxic cultures, hMSCs may be cultured at 95% air (20% $O_7$)—5% $CO_2$. For hypoxia studies, hMSCs may be cultured in the custom-made cell culture chambers that are flushed with humidified gas mixtures of three different oxygen compositions: 1% $O_2$—5% $CO_2$—94% $N_2$, 2% $O_2$—5% $CO_2$—93% $N_2$, and 3% $O_2$—5% $CO_2$—92% $N_2$. hMSC may be continuously cultured under these conditions for up to 30 passages. We have successfully used these cell culture chambers in our prior studies (Grayson et al., 2006; Grayson et al., 2007).

hMSC Seeding and Growth in the 3D Perfusion Bioreactor.

The in-house 3D PET perfusion bioreactor system may be modified with addition of gas pouch on each side of the chamber to control $O_2$ and pH using gas mixture (FIG. 1). The system with 4 individual chambers may be used for the experiments, following an established procedure in our lab (Zhao et al., 2009; U.S. Pat. No. 6,875,605; U.S. Pat. No. 6,943,008; Zhao et al., 2005). Spatial distribution after cell seeding may be determined by histology and cell growth may be determined by DNA assay.

Decellularization of 3D Construct by Perfusion.

At days 14 and 21 after seeding, the media may be removed from the bioreactor chambers. By operating the bioreactor in TF, the constructs will be first washed with PBS, then the decellularization solution containing Triton-X and $NH_4OH$ in PBS, and finally the solution containing DNase. The composition of the perfusion decellularized constructs may be analyzed using ELISA and Western blot. Based on the results, the effects of flow rate and incubation time on ECM composition may be evaluated.

hMSC Re-Seeding and Long-Term Expansion.

After decellularization, the freshly isolated hMSC at a predetermined density may be re-seeded in each chamber at a flow rate of 0.1 mL/min and continuously cultured. At days 1, 7, 14, and 21 after re-seeding, one chamber may be removed at each day to collect cell samples. Day 1 samples may be used to determine re-seeding efficiency and spatial distribution while the subsequent samples for cellular and molecular assays.

Control Experiments and Statistical Comparison.

Parallel to the perfusion bioreactor with decellularized matrices, both (1) PET bioreactor control and (2) ECM control experiments can be carried out for comparison. In PET bioreactor control, hMSC at same passage and density are seeded onto PET scaffolds alone and culture under same oxygen tension and sampled over same period. For the ECM control experiments, hMSC are seeded onto the hMS C-derived ECM matrices on TP and cultured under same oxygen condition.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 6,875,605
U.S. Pat. No. 6,943,008
U.S. Pat. No. 5,486,359
Afzal M R, Haider H K, Idris N M, Jiang S, Ahmed R P and Ashraf M. Preconditioning Promotes Survival and Angiomyogenic Potential of Mesenchymal Stem Cells in the Infarcted Heart via NF-KB Signaling. *Antioxidants & Redox Signaling.* 2010, 12, 693-702.
Aggarwal S., and Pittenger M F. Human mesenchymal stem cells modulate allogeneic immune cell responses. *Blood*, 2005, 105, 1815-22.
Ankeny D P, McTigue D M, Jakeman L B. Bone marrow transplants provide tissue protection and directional guidance for axons after contusive spinal cord injury in rats. *Exp. Neurol,* 2004, 190, 17-31.
Attwell S, Roskelley C and Dedhar S. The integrin-linked kinase (ILK) suppresses anoikis. *Oncogene.* 2000, 19, 3811-3815.
Baksh D, Zandstra P W, and Davies J E. A Non-Contact Suspension Culture Approach to the Culture of Osteogenic Cells Derived from a CD49elow Subpopulation of Human Bone Marrow-Derived Cells. *Biotechnol. Bioeng.* 2007, 98, 1195-1208.
Banfi A, Muraglia A, Dozin B, Mastrogiacomo M, Cancedda R, Quarto R. Proliferation kinetics and differentiation potential of ex vivo expanded human bone marrow stromal cells: implications for their use in cell therapy. *Experimental Hematology.* 2000, 28, 707-715.
Barbash I M, Chouraqui P, Baron J, Feinberg M S, Etzion S, Tessone A, Miller L, Guetta E, Zipori D, Kedes L H, Kloner R A, Leor J. Systemic delivery of bone marrow-derived mesenchymal stem cells to the infracted myocardium: feasibility, cell migration, and body distribution. *Circulation.* 2003, 108, 863-868.
Bernardo M E, Zaffaroni N, Novara F, Cometa A M, Avanzini M A, Moretta A, Montagna D, Maccario R, VIIIa R, Daidone M G, Zuffardi O, and Locatelli F. Human bone marrow derived mesenchymal stem cells do not undergo transformation after long-term in vitro culture and do not exhibit telomeremaintenance mechanisms. *Cancer Res,* 2007, 67, 9142-9149.
Bruder S. P., N. Jaiswal, S. E. Haynesworth. Growth kinetics, self-renewal, and the osteogenic potential of purified human mesenchymal stem cells during extensive subcultivation and following cryopreservation. *J. Cell. Biochem.* 1997, 64, 278-294.
Buravkova L B and Anokhina E B. Effect of hypoxia on stromal precursors from rat bone marrow at the early stage of culturing. *Bulletin of Experimental Biology and Medicine.* 2007, 143, pp. 411-413.

Caplan A I and Dennis J E. Mesenchymal Stem Cells as Trophic Mediators. *Journal of Cellular Biochemistry.* 2006, 98, 1076-1084.

Carcamo-Orive I, Tejados N, Delgado J, Gaztelumendi A, Otaegui D, Lang V, and Trigueros C. ERK2 protein regulates the proliferation of human mesenchymal stem cells without affecting their mobilization and differentiation potential. *Experimental Cell Research.* 2008, 314, 1777-1788.

Chen J, Sanberg P R, Li Y, Wang L, Lu M, Willing A E, Sanchez-Ramos J, and Chopp M Intravenous administration of human umbilical cord blood reduces behavioral deficits after stroke in rats. *Stroke,* 2001, 2682-2688.

Chen S L, Fang W W, Ye F, Liu Y H, Qian J, Shan S J, Zhang J J, Chunhua R Z, Liao L M, Lin S, and Sun J P. Effect on Left Ventricular Function of Intracoronary Transplantation of Autologous Bone Marrow Mesenchymal Stem Cell in Patients With Acute Myocardial Infarction. *Am J Cardiol.* 2004, 94, 92-95.

Chen X D, Deusevich V, Feng J Q, Manolagas S C, and Jilka R L. Extracellular Matrix Made by Bone Marrow Cells Facilitates Expansion of Marrow-Derived Mesenchymal Progenitor Cells and Prevents Their Differentiation Into Osteoblasts. *J Bone Miner Res.* 2007, 22, 1943-1956.

Cukierman E, Pankov R and Yamada K M. Cell interactions with three-dimensional matrices. *Current Opinion in Cell Biology.* 2002, 14, 633-639.

Cukierman E, Pankov R, Stevens D R, Yamada K M. Taking cell-matrix adhesions to the third dimension. *Science.* 2001, 14, 1708-1712.

Damianova R, Stefanova N, Cukierman E, Momchilova A, Pankov R. Three-dimensional matrix induces sustained activation of ERK1/2 via Src/Ras/Raf signaling pathway. *Cell Biology International.* 2008, 32, 229-234.

Datta S R, Brunet A and Greenberg M E. Cellular survival: a play in three Akts. *Genes and Development.* 1999, 13, 2905-2927.

Dennis J E, Esterly K, Awadallah A, Parrish C R, Poynter G M, and Goltry K L. Clinical-Scale Expansion of a Mixed Population of Bone Marrow-Derived Stem and Progenitor Cells for Potential Use in Bone Tissue Regeneration. *Stem Cells.* 2007, 25, 2575-2582.

Dezawa M, Takahashi I, Esaki M, Takano M, and Sawaka H. Sciatic nerve regeneration in rats induced by transplantation of in vitro differentiated bone-marrow stromal cells. *Eur J. Neurosci,* 2001, 14, 1171-1176.

D'Ippolito G, Howard G A, Roos B A, and Schiller P C. Sustained stromal stem cell self-renewal and osteoblastic differentiation during aging. *Rejuvenation Res* 2006, 9, 10-19.

Discher D E, Mooney, D J, and Zandstra P W. Growth factors, mat4rices, and forces combine and control stem cells. *Science.* 2009, 324, 1673-1677.

Fehrer C, Brunauer R, Laschober G, Unterluggauer H, Reitinger S, Kloss F, Gülly C, Gassner R, Lepperdinger G. Reduced oxygen tension attenuates differentiation capacity of human mesenchymal stem cells and prolongs their lifespan. *Aging Cell,* 2007, 6, 745-757.

Ferrari G, Cusella-De Angelis G, Coletta M, Paolucci E, Stornaiuolo A, Cossu G, and Mavillio F. Muscle regeneration by bone marrow-derived myogenic progenitors. *Science,* 1998, 1528-1530.

Furlani D, Ugurlucan M, Ong L L, Bieback K, Pittermann E, Westien I, Wang W W, Yerebakan C, Li W Z, Gaebel R, Li R K, Vollmar B, Steinhoff G, Ma N. Is the intravascular administration of mesenchymal stem cells safe? Mesenchymal stem cells and intravital microscopy. *Microvascular Research.* 2009, 77, 370-376.

Gnecchi M, He H M, Noiseux N, Liang O D, Zhang L, Morello F, Nu H, Melo L G, Pratt R E, Ingwall J S, and Dzau V J. Evidence supporting paracrine hypothesis for Akt-modified mesenchymal stem cell-mediated cardiac protection and functional improvement. *FASEB J.* 2006, 20, pp. 661-669.

Grayson W L, Ma T and Bunnell B. Human Mesenchymal Stem Cells Tissue Development in 3D PET Matrices. *Biotechnology Progress,* 2004, 20, 905-912.

Grayson W L, Zhao F, Bunnell B and Ma T. Hypoxia enhances proliferation and tissue formation of human mesenchymal stem cells. *Biochem Biophys Res Commun.* 2007, 948-953.

Grayson W L, Zhao F, Izadpanah R, Bunnell B, Ma T. Effects of hypoxia on human mesenchymal stem cell expansion and plasticity in 3D constructs. *J. Cell. Physiol* 2006, 207, 331-339.

Hofstetter C P, Schwarz E J, Hess D, Widenfalk J, E L Manira A, Prockop D J, and Olson L. Marrow stromal cells form guiding strands in the injured spinal cord and promote recovery. *Proc Natl Acad Sci USA* 2002, 99(4), 2199-2204.

Homsy C A, McDonald K E, Akers W W, Short C, Freeman B S. Surgical Suture-Canine Tissue Interaction for Six Common Suture Types. *J Biomed Mater Res.* 1968, 2, 215.

Honczarenko M, Le Y, Swerkowski M, Ghiran I, Glodek A M, and Silberstein L E. Human bone marrow stromal cells express a distinct set of biologically functional chemokine receptors. *Stem Cells.* 2006, 24, 1030-1041.

Illingworth B, Tweden K, Schroeder R, Cameron J D. In Vivo Efficacy of Silver-Coated (Silzone) Infection-Resistant Polyester Fabric Against a Biofilm-Producing Bacteria, *Staphylococcus Epidermidis. J Heart Valve Dis.* 1998, 7, 524-530.

Karp J M and Teo G S L. Mesenchymal stem cell homing: the devil is in the details. *Cell Stem Cell.* 2009, 206-216.

Katritsis D G, Sotiropoulou P A, Karvouni E, Karabinos I, Korovesis S, Perez S A, Voridis E M, Papamichail M. Transcoronary transplantation of autologous mesenchymal stem cells and endothelial progenitors into infarcted human myocardium. *Catheter Cardiovasc Interv.* 2005, 65, 321-329.

Keith B, Simon M C. Hypoxia-inducible factors, stem cells, and cancer. *Cell.* 2007, 129, 465-472.

Kertlow J D, Jin Y Q, Liu W, Zhang W J, Hong T H, Zhou G, Baggett L S, Mikos A G, Cao Y L. Donor age and cell passage affects differentiation potential of murine bone marrow-derived stem cells. *BMC Cell Biology,* 2008, 9, 60.

Klees R F, Salasznyk R M, Kingsley K, Williams W A, Boskey, A, and Plopper G E. Laminin-5 induces osteogenic gene expression in human mesenchymal stem cells through an ERK-dependent pathway. *Mol. Biol. Cell.* 2005, 16, 881.

Klein G. The extracellular matrix of the hematopoietic microenvironment. *Experientia.* 1995, 51, 914-926.

Klinge U, Klosterhalfen B, Conze J, Limberg W, Obolenski B, Ottinger A P, Schumpelick V. Modified Mesh for Hernia Repair that is Adapted to the Physiology of the Abdominal Wall. *Eur J Surg.* 1998, 164, 951-960.

Koc O N, Gerson S L, Cooper B W, Dyhouse S M, Haynesworth S E, Caplan A I, and Lazarus H M. Rapid hematopoietic recovery after coinfusion of autologous-blood stem cells and culture-expanded marrow mesenchymal stem cells in advanced breast cancer patients receiving high-dose chemotherapy. *J Clin Oncol.* 2000, 18, 307-316.

Kofoed H, Sjontoft E, Siemssen S O, Olesen H P. Bone-marrow circulation after osteotomy—blood flow, $pO_2$, $pCO_2$, and pressure studied in dogs. *Acta Orthop Scand.* 1985, 56, 400-403.

Kuhn N Z and Tuan R S. Regulation of Sternness and Stem Cell Niche of Mesenchymal Stem Cells: Implications in Tumorigenesis and Metastasis. *J Cell Physiol.* 2010, 222, 268-277.

Kundu A K and Putnam A J. Vitronectin and collagen I differentially regulate osteogenesis in mesenchymal stem cells. *Biochemical and Biophysical Research Communications.* 2006, 347, 347-357.

Kundu A K, Khatiwala C B and Putnam A J. Extracellular Matrix Remodeling, Integrin Expression, and Downstream Signaling Pathways Influence the Osteogenic Differentiation of Mesenchymal Stem Cells on Poly(Lactide-Co-Glycolide) Substrates. *Tissue Engineering: Part A.* 2009, 15, 273-283.

Lasala G P, Silva J A, Gardner P A, and Minguell J J. Combination Stem Cell Therapy for the Treatment of Severe Limb Ischemia: Safety and Efficacy Analysis. *Angiology.* 2010, 61(6), 551-556.

Lazarus H M, Koc O N, Devine S M, Curtin P, Maziarz R T, Holland H K, Shpall E J, McCarthy P, Atkinson K, Cooper B W, Gerson S L, Laughlin M J, Loberiza F R Jr, Moseley A B, Bacigalupo A. Cotransplantation of HLA-identical sibling culture-expanded mesenchymal stem cells and hematopoietic stem cells in hematologic malignancy patients. *Biol Blood Marrow Transplant.* 2005, 11, 389-398.

Le Blanc K, Tammik L, Sundberg B, HaynesworthS E, and Ringden O. Mesenchymal stem cells inhibit and stimulate mixed lymphocyte cultures and mitogenic responses independently of the major histocompatibility complex. *Scand J. Immunol,* 2003, 11-20.

Lee J S, Hong J H, Moon G J, Lee P H, Alm Y H, and Bang O Y. A Long-Term Follow-Up Study of Intravenous Autologous Mesenchymal Stem Cell Transplantation in Patients With Ischemic stroke. *Stem Cells.* 2010, 28, 1099-1106.

Lennon D P, Edmison J M, Caplan A I. Cultivation of rat marrow-derived mesenchymal stem cells in reduced oxygen tension: Effects on in vitro and in vivo osteochondrogenesis. *J. Cell Physiol.* 2001, 187, 345-355.

Li W U, Choi Y J and Lee P H, Huh K, Kang Y M, Kim H S, Aim Y H, Lee G, and Bang O Y. Mesenchymal stem cells for ischemic stroke: changes in effects after ex vivo culturing. *Cell Transplantation.* 2008, 17, 1045-1059.

Li Y, Ma T, Kniss D A, Lasky L C, Yang S T. Effects of Filtration Seeding on Cell Density, Spatial Distribution, and Proliferation in Nonwoven Fibrous Matrices. *Biotechnol. Prog.,* 2001, 17, 935-944.

Liao T, Moussallem M D, Kim J, Schlenoffd J B, Ma T. N-Isopropylacrylamide-Based Thermoresponsive Polyelectrolyte Multilayer Films for Human Mesenchymal Stem Cell Expansion. *Biotechnol. Prog.,* 2010, 26, 1705-1713.

Liechty K W, MacKenzie T C, Shaaban A F, Radu A, Moseley A B, Deans R, Marshak D R, and Flake A W. Human mesenchymal stem cells engraft and demonstrate site-specific differentiation after in utero transplantation in sheep. *Nature Medicine,* 2000, 6, 1282-1286.

Lund A W, Yener B, Stegemann J P, Plopper G E. The Natural and Engineered 3D Microenvironment as a Regulatory Cue During Stem Cell Fate Determination. *Tissue Engineering Part B.* 2009, Vol. 15, 3, pp. 371-380.

Mangi A A, Noiseux N, Kong D, He H M, Rezvani M, Ingwall J S, Dzau V J. Mesenchymal stem cells modified with Akt prevent remodeling and restore performance of infarcted hearts. *Nature Medicine.* 2003, 9, 1195-1201.

Marolt D, Knezevic M, and Novakovic G V. Bone tissue engineering with human stem cells. *Stem Cell Research and Therapy.* 2010, 1, 10.

Meloche S and Pouyssegur J. The ERK1/2 mitogen-activated protein kinase pathway as a master regulator of the G1- to S-phase transition. *Oncogene.* 2007, 26, 3227-3239.

Nagaya N, Kangawa K, Itoh T, Iwase T, Murakami S, Miyahara Y, Fujii T, Uematsu M, Ohgushi H, Yamagishi M, Tokudome T, Mori H, Miyatake K, Kitamura S. Transplantation of mesenchymal stem cells improves cardiac function in a rat model of dilated cardiomyopathy. *Circulation.* 2005, 112, 1128-1135.

Ohgushi H, Goldberg V M and Caplan A I. Repair of bone defects with marrow cells and porous ceramic. Experiments in rats. *Acta Orthop Scand.* 1989, 60(3), 334-339.

Pereira R F, O'Hara M D, Laptev A V, Halford K W, Pollard M D, Class R, Simon D, Livezey K, and Prockop D J. Marrow stromal cells as a source of progenitor cells for nonhematopoietic tissues in transgenic mice with a phenotype of osteogenesis imperfecta. *Proc Natl Acad Sci USA.* 1998, 95(3), 1142-1147.

Potier E, Ferreira E, Andriamanalijaona R, Pujol J P, Oudina K, Logeart-Avramoglou D, Petite H. Hypoxia affects mesenchymal stromal cell osteogenic differentiation and angiogenic factor expression. *Bone,* 2007, 40, 1078-1087.

Prockop D J and Olson S D. Clinical trials with adult stem/progenitor cells for tissue repair: let's not overlook some essential precautions. *Blood.* 2007, 3147-3151.

Prockop D J, Brenner M, Fibbe W E, Horwitz E, Le Blanc K, Phinney D G, Simmons P J, Sensebe L, and Keating A. Defining the risks of mesenchymal stem cell therapy. *Cytotherapy.* 2010, 12(5), 576-578.

Prockop D J. Repair of Tissues by Adult Stem/Progenitor Cells (MSCs): Controversies, Myths, and Chaning Paradigms. *Molecular Therapy.* 2009, 17(6), 939-946.

Quarto R, Mastrogiacomo M, Cancedda R, Kutepov S M, Mukhachev V, Lavroukov A, Kon E, Marcacci M. Repair of large bone defects with the use of autologous bone marrow stromal cells. *N Engl J Med.* 2001, 344, 385-386.

Rayment E A and Williams D J. Concise Review: Mind the Gap: Challenges in Characterizing and Quantifying Cell- and Tissue-Based Therapies for Clinical Translation. *Stem Cells.* 2010, 28, pp. 996-1004.

Riepe G, Loos J, Imig H, Schröder A, Schneider E, Petermann J, Rogge A, Ludwig M, Schenke A, Nassutt R, Chakfe N, Morlock M. Long-term in vivo Alterations of Polyester Vascular Grafts in Humans. *Eur J Vase Endovasc Surg.* 1997, 13, 540-548.

Rombouts W J C and Ploemacher R E. Primary murine MSC show highly efficient homing to the bone marrow but lose homing ability following culture. *Leukemia.* 2003, 17, 160-170.

Rosova I, Dao M, Capoccia B, Link D, Nolta J A. Hypoxic Preconditioning Results in Increased Motility and Improved Therapeutic Potential of Human Mesenchymal Stem Sackstein R, Merzaban J S, Cain D W, Dagia N M, Spencer J A, Lin C P, and Wohlgemuth R. Ex vivo glycan engineering of CD44 programs human multipotent mesenchymal stromal cell trafficking to bone. *Nature Medicine.* 2008, 14, 181-187.

Sadat S, Gehmert S, Song Y H, Yen Y, Bai X, Gaiser S, Klein H, Alt E. The cardioprotective effect of mesenchymal stem cells is mediated by IGF-1 and VEGF. *Biochem Biophys Res Commun.* 2007, Vol. 363, pp. 674-679.

Sakai D, Mochida J, Iwashina T, Hiyama A, Omi H, Imai M, Nakai T, Ando K, Hotta T. Regenerative effects of transplanting mesenchymal stem cells embedded in collagen to the degenerated intervertebral disc. *Biomaterials.* 2006, 27, 335-345.

Salasznyk R M, Klees R F, Hughiock M K, and Plopper G E. ERK signaling pathways regulate the osteogenic differentiation of human mesenchymal stem cells on collagen I and vitronectin. *Cell Commun Adhes.* 2004, 11, 137.

Salem H K and Thiemermann C. Mesenchymal Stromal Cells: Current Understanding and Clinical Status. *Stem Cells.* 2010, 28, 585-596.

Sharrocks A D. Cell Cycle: Sustained ERK Signalling Represses the Inhibitors. *Current Biology.* 2006, 16, R540-2.

Simmons C A, Matlis S, Thornton A J, Chen S, Wang C Y, Mooney D J. Cyclic strain enhances matrix mineralization by adult human mesenchymal stem cells via the extracellular signal-regulated kinase (ERK1/2) signaling pathway. *Journal of Biomechanics.* 2003, 36, 1087-1096.

Smith D M, Goltry, K L, Dennis J E, Bartel R L, and Rowley J A. Adult Stem Cell Therapies for Tissue Regeneration: Ex Vivo Expansion in an Automated System. *Stem Cells Research and Therapeutics.* (Editors: Y Shi and D O Clegg) Springer Science+Business, 2008.

Soares B, Guidoin R G, Marois Y, Martin L, King M W, Laroche G, Zhang Z, Charara J, Girard J F. In vivo characterization of a fluoropassivated gelatin-impregnated polyester mesh for hernia repair. *J Biomed Mater Res.* 1996, 32, 293-305.

Son B R, Marquez-Curtis L A, Kucia M, Wysoczynski M, Tuner A R, Ratajczak J, Ratajczak M Z, Janowska-Wieczorek A. Migration of bone marrow and cord blood mesenchymal stem cells in vitro is regulated by stromal-derived factor-1-CXCR4 and hepatocyte growth factor-cmet axes and involves matrix metalloproteinases. *Stem Cells.* 2006, 24, 1254-1264.

Sykova E, Jendelova P, Urdzikova L, Lesny P, and Hejcl A. Bone marrow stem cells and polymer hydrogels—two strategies for spinal cord injury repair. *Cell Mol. Neurobiol.* 2006, 26, 1113-1129.

Tang Y, Yasuhara T, Koichi H, Matsukawa N, Naki M, Yu G, Su L, Hess D C, and Borlongan C V. Transplantation of Bone Marrow-Derived Stem Cells: A Promising Therapy for Stroke. *Cell Transplantation.* 2007, 16, 159-169.

Toma C, Wagner W R, Bowry S, Schwartz A, and Villanueva F. Fate of culture-expanded mesenchymal stem cells in the microvasculature. *Circulation Research,* 2009, 398-402.

Tweden K, Cameron J D, Razzouk A, Holmberg W, Kelly S. Biocompatibility of Silver-Modified Polyester for Antimicrobial Protection of Prosthetic Valves. *J Heart Valve Dis.* 1997, 6, 553-561.

Vinard E, Eloy R, Descotes J, Brudon J R, Guidicelli H, Magne J L, Patra P, Berruet R, Huc A, Chauchard J. Stability of performances of vascular prostheses retrospective study of 22 cases of human implanted prostheses. *J Biomed Mater Res.* 1988, 22, 633-648.

Wall M E, Bernacki S H, and Loboa E G. Effects of serial passaing on the adipogenic and osteogenic differentiation potential of adipose-derived human mesenchymal stem cells. *Tissue Eng.,* 2007, 1291-1298.

Wang Z J, Zhang F M, Wang L S, Yao Y W, Zhao Q, and Gao X. Lipopolysaccharides can protect mesenchymal stem cells (MSCs) from oxidative stress-induced apoptosis and enhance proliferation of MSCs via Toll-like receptor (TLR)-4 and PI3K/Akt. *Cell Biology International.* 2009, 33, 665-674.

Xian C J and Foster B K. Repair of injured articular and growth plate cartilage using mesenchymal stem cells and chondrogenic gene therapy. *Curr Stem Cell Res Ther.* 2006, 1, 213-229.

Yang Y, Rolls F M V, and Putnins E E. Ex vivo expansion of rat bone marrow mesenchymal stromal cells on microcarrier beads in spin culture. *Biomaterials.* 2007, 28, 3110-3120.

Zhang M, Mal N, Kiedrowski M, Chacko M, Askari A T, Popovic Z B, Koc O N, and Penn M S. SDF-1 expression by mesenchymal stem cells results in trophic support of cardiac myocytes after myocardial infarction. *FASEB J.* 2007, 21, 3197-3207.

Zhao F and Ma T. Perfusion bioreactor system for human mesenchymal stem cell tissue engineering: Dynamic cell seeding and construct development. *Biotechnol Bioeng,* 2005, 91, 482-493.

Zhao F, Chella R and Ma T. Effects of Shear Stress on 3-D Human Mesenchymal Stem Cell Construct Development in a Perfusion Bioreactor System: Experiments and Hydrodynamic Modeling. *Biotechnol Bioeng.,* 2007, 96, 584-595.

Zhao F, Grayson W L and Ma T. Perfusion Bioreactor Affects the Nuclear Shape and ECM Structure of Human Mesenchymal Stem Cells in 3D Scaffolds. *J. Cell. Physiol* 2009, 219, 421-429.

Zhao F, Pathi P, Grayson W, Xing Q, Locke B, and Ma T. Effects of Oxygen Transport on 3-D Human Mesenchymal Stem Cell Metabolic Activity in Perfusion and Static Cultures Experiments and Mathematical Model. *Biotechnology Progress.* 2005, 21, 1269-1280.

We claim:

1. A method for growing and/or expanding mammalian mesenchymal stem cell (MSC), the method comprising:
   a) seeding freshly isolated mammalian MSC on a planar surface or a porous three-dimension (3-D) scaffold, wherein said surface or scaffold comprises one or more thermally responsive films or coatings;
   b) growing said mammalian MSC under an $O_2$ tension that is lower than 20%;
   c) decellularizing said surface or scaffold; and
   d) reseeding said surface or scaffold with freshly isolated mammalian MSC, whereby said reseeded mammalian MSC grow and maintain an undifferentiated phenotype.

2. The method of claim 1, wherein said $O_2$ tension is between about 1% and 10%; or about 1% and 5%; or about 1% and 3%; or is about 2%.

3. The method of claim 1, wherein said decellularizing step is performed using a detergent and an enzyme that degrades nucleic acid.

4. The method of claim 1, further comprising the step of harvesting said reseeded MSC from said surface or scaffold.

5. The method of claim 1, wherein said mammalian MSC are human MSC.

6. The method of claim 1, wherein said mammalian MSC are isolated from bone marrow or adipose tissue of a mammal.

7. The method of claim 1, wherein said surface or scaffold is non-degradable.

8. The method of claim 1, wherein said surface or scaffold is composed of one or more of poly(styrene), poly(carprolactone), nylon, or poly(ethylene terephthalate) (PET).

9. The method of claim 1, wherein said reseeded cells are allowed to grow on said surface or scaffold for up to about three months.

10. The method of claim 1, wherein said thermally responsive film or coating comprises one or more of N-isopropylacrylamide, poly(allylamine hydrochloride)-co-poly(N-isopropylacrylamide), or poly(styrene sulfonate)-co-poly(N-isopropylacrylamide).

11. The method of claim 1, wherein said one or more thermally responsive films or coatings comprises a terminal layer of positively charged allylamine hydrochloride (PAH), or negatively charged styrene sulfonic acid (PSS), or serum.

12. The method of claim 1, wherein said reseeded MSC are harvested from said surface by modulating the temperature of said thermally responsive film or coating to a temperature where cells adhered thereto are released.

13. The method of claim 12, wherein said harvested MSC are further grown and cultivated in suspension culture.

14. The method of claim 1, wherein said MSC are grown on said scaffold in a perfusion bioreactor.

15. The method of claim 1, wherein said MSC are grown in cell culture media comprising an animal serum at a concentration less than about 5% v/v or in serum-free cell culture media.

16. A composition comprising a decellularized extracellular matrix (ECM) prepared in vitro by:
   a) seeding freshly isolated mammalian MSC on a planar surface or a porous three-dimension (3-D) scaffold, wherein said surface or scaffold comprises one or more thermally responsive films or coatings;
   b) growing said mammalian MSC under an $O_2$ tension that is lower than 20%; and
   c) decellularizing said surface or scaffold.

17. The composition of claim 16, wherein said $O_2$ tension is between about 1% and 10%; or about 1% and 5%; or about 1% and 3%; or is about 2%.

18. The composition of claim 16, wherein said decellularizing step is performed using a detergent and an enzyme that degrades nucleic acid.

19. The composition of claim 16, wherein said surface or scaffold is composed of one or more of poly(styrene), poly(carprolactone), nylon, or poly(ethylene terephthalate) (PET).

20. The composition of claim 16, wherein said thermally responsive film or coating comprises one or more of N-isopropylacrylamide, poly(allylamine hydrochloride)-co-poly(N-isopropylacrylamide), or poly(styrene sulfonate)-co-poly(N-isopropylacrylamide).

21. The composition of claim 16, wherein said one or more thermally responsive films or coatings comprises a terminal layer of positively charged allylamine hydrochloride (PAH), or negatively charged styrene sulfonic acid (PSS), or serum.

22. A composition comprising a decellularized extracellular matrix (ECM) prepared in vitro by:
   a) seeding freshly isolated mammalian MSC on a planar surface or a porous three-dimension (3-D) scaffold, wherein said surface or scaffold is composed of one or more of poly(styrene), poly(carprolactone), nylon, or poly(ethylene terephthalate) (PET);
   b) growing said mammalian MSC under an $O_2$ tension that is lower than 20%; and
   c) decellularizing said surface or scaffold.

* * * * *